(12) United States Patent
Doudna et al.

(10) Patent No.: US 12,227,547 B2
(45) Date of Patent: Feb. 18, 2025

(54) MODULATORS OF CAS9 POLYPEPTIDES AND METHODS OF USE THEREOF

(71) Applicant: The Regents of the University of California, Oakland, CA (US)

(72) Inventors: Jennifer A. Doudna, Berkeley, CA (US); Kyle E. Watters, Moraga, CA (US); Haridha Shivram, Berkeley, CA (US); Christof Fellmann, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1033 days.

(21) Appl. No.: 17/270,691

(22) PCT Filed: Sep. 9, 2019

(86) PCT No.: PCT/US2019/050214
§ 371 (c)(1),
(2) Date: Feb. 23, 2021

(87) PCT Pub. No.: WO2020/055748
PCT Pub. Date: Mar. 19, 2020

(65) Prior Publication Data
US 2021/0340199 A1   Nov. 4, 2021

Related U.S. Application Data

(60) Provisional application No. 62/729,295, filed on Sep. 10, 2018.

(51) Int. Cl.
*C07K 14/47* (2006.01)
*C12N 9/22* (2006.01)
*C12N 15/113* (2010.01)

(52) U.S. Cl.
CPC .......... *C07K 14/4703* (2013.01); *C12N 9/22* (2013.01); *C12N 15/1137* (2013.01); *C07K 2319/09* (2013.01); *C07K 2319/40* (2013.01); *C12Y 301/00* (2013.01)

(58) Field of Classification Search
None
See application file for complete search history.

(56) References Cited

U.S. PATENT DOCUMENTS

| 2006/0115490 A1 | 6/2006 | Masignani |
| 2018/0251792 A1 | 9/2018 | Friedland et al. |

FOREIGN PATENT DOCUMENTS

| WO | WO 2017/160689 | 9/2017 | |
| WO | WO 2018/197495 A1 | 11/2018 | |
| WO | WO 2019185751 | * 10/2019 | ........... C07K 14/195 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Basgall, et al.; "Gene drive inhibition by the anti-CRISPR proteins AcrIIA2 and AcrIIA4 in *Saccharomyces cerevisiae*"; Microbiology; vol. 164, pp. 464-474 (2018).
Hynes, et al.; "Widespread anti-CRISPR proteins in virulent bacteriophages inhibit a range of Cas9 proteins"; Nature Communications; vol. 9, No. 2919, 10 pages (2018).
Kim, et al.; "Solution structure and dynamics of anti-CRISPR AcrIIA4, the Cas9 inhibitor"; Scientific Reports; vol. 8, No. 3883, pp. 1-9 (Mar. 1, 2018).
Pawluk, et al.; "Naturally occurring off-switches for CRISPR-Cas9"; Cell; vol. 167, No. 7, pp. 1829-1838 (Dec. 8, 2016).
Shin, et al.; "Disabling Cas9 by an anti-CRISPR DNA mimic"; Science Advances; vol. 3, No. 7, pp. 1-9 (Jul. 12, 2017).
Hynes, et al.; "An anti-CRISPR from a virulent streptococcal phage inhibits *Streptococcus pyogenes* Cas9"; Nature Microbiology; vol. 2, pp. 1374-1380 (2017).

* cited by examiner

*Primary Examiner* — Richard G Hutson
(74) *Attorney, Agent, or Firm* — James J. Diehl; Bozicevic, Field & Francis LLP

(57) ABSTRACT

The present disclosure provides AcrIIA7 polypeptides, nucleic acids encoding the AcrIIA7 polypeptides, and kits comprising the AcrIIA7 polypeptides and/or nucleic acids encoding the ACRIIA7 polypeptides. The present disclosure provides methods of inhibiting an activity of a Cas9 polypeptide.

22 Claims, 16 Drawing Sheets

Specification includes a Sequence Listing.

FIG. 1

AcrIIA7 amino acid sequence

MRETIQRLLASNLSSNSIALATGVSQAVISKLRNAKKEIGNLSLNSAEKLYNYQKGLEVMNKSIEIKDQNNIVLIDSLGQFFTDIENDNNGRYNIDYVLLNEVE HDNGNTYYEVGMYRTEEVPFSDKVTQDNVELLEDKWLQIDQQGESYVESIFFENEEDAREYIKLVLKGHETFEETAKAIGVIK (SEQ ID NO:1)

FIG. 2

AcrIIA7 human optimized nucleic acid sequence

ATGAGGGAAACAATTCAAGGCTGCTCGCGTCTAACCTCAGTAGCAATTCAATCGCTTTGGCCACAGGCGTAAGCCAGGCAGTTATTAGCAAACTG
CGGAATGCCAAAAAGAGAGATAGGCAACCTTTCTCAATAGCGCGGAAAAGTTGTATAATTACCAGAAGGGCCTGAAGTCATGAACAAATCTATC
GAGATCAAAGATCAAAACAACATAGTCCTGATTGACAGTCTTGGACAGTTCTTACAGACATCGAAAATGATAATAACGGTCGATATAACATCGAC
TACGTGCTGTCAACGAGGTAGAACACGAACACAATGGCAACACGTACTACGAAGTGGGCATGTATCGGACCGAAGAGGTACCCTTTCCGACAAAGT
GACCCAGGACAATGTGATAGACTTCTGGAGGATAAATGGCTGCAAATAGATCAACAAGGGCGAGAGCTATGTTGAAAAGCATTTTTTTGAGAACGAAG
AGGACGCTAGAGAGAATATATTAAGTTGGTCCTGAAGGGTCATGAGACATTTGAGGAAACGGCTAAAGCAATCGGAGTCATCAAGTAA (SEQ ID NO:2)

FIG. 3

SauCas9 amino acid

MGKRNYILGLDIGITSVGYGIIDYETRDVIDAGVRLFKEANVENNEGRRSKRGARRLKRRRRHRIQRVKKLLFDYNLLTDHSELSGINP
YEARVKGLSQKLSEEEFSAALLHLAKRRGVHNVNEVEEDTGNELSTKEQISRNSKALEEKYVAELQLERLKKDGEVRGSINRFKTSDYV
KEAKQLLKVQKAYHQLDQSFIDTYIDLLETRRTYYEGPGEGSPFGWKDIKEWYEMLMGHCTYFPEELRSVKYAYNADLYNALNDLNNLV
ITRDENEKLEYYEKFQIIENVFKQKKKPTLKQIAKEILVNEEDIKGYRVTSTGKPEFTNLKVYHDIKDITARKEIENAELLDQIAKIL
TIYQSSEDIQEELTNLNSELTQEEIEQISNLKGYTGTHNLSLKAINLILDELWHTNDNQIAIFNRLKLVPKKVDLSQQKEIPTTLVDDF
ILSPVVKRSFIQSIKVINAIIKKYGLPNDIIIELAREKNSKDAQKMINEMQKRNRQTNERIEEIIRTTGKENAKYLIEKIKLHDMQEGK
CLYSLEAIPLEDLLNNPFNYEVDHIIPRSVSEDNSFNNKVLVKQEENSKKGNRTPFQYLSSDSKISYETFKKHILNLAKGKGRISKTK
KEYLLEERDINRFSVQKDFINRNLVDTRYATRGLMNLLRSYFRVNNLDVKVKSINGGFTSFLRRKWKFKERNKGYKHHAEDALIIANA
DFIFKEWKKLDKAKKVMENQMFEEKQAESMPEIETEQEYKEIFITPHQIKHIKDFKDYKYSHRVDKKPNRELINDTLYSTRKDKGNTL
IVNNLGLYDKDNDKLKKLINKSPEKLLMYHHDPQTYQKLKLIMEQYGDEKNPLYKYEETGNYLTKYSKKDNGPVIKKIKYYGNKLNA
HLDITDDYPNSRNKVVKLSLKPYRFDVYLDNGVYKFVTVKNLDVIKKENYYEVNSKCYEEAKKLKKISNQAEFIASFYNNDLIKINGEL
YRVIGVNNDLLNRIEVNMIDITYREYLENMNDKRPPRIKTIASKTQSIKKYSTDILGNLYEVKSKKHPQIIKKG (SEQ ID NO:3)

FIG. 4

SpyCas9 amino acid

MDKKYSIGLDIGTNSVGWAVITDEYKVPSKKFKVLGNTDRHSIKKNLIGALLFDSGETAEATRLKRTARRRYTRRKNRICYLQEIFSNEMAKVDDSFFHRLEE
SFLVEEDKKHERHPIFGNIVDEVAYHEKYPTIYHLRKKLVDSTDKADLRLIYLALAHMIKFRGHFLIEGDLNPDNSDVDKLFIQLVQTYNQLFEENPINASGVD
AKAILSARLSKSRRLENLIAQLPGEKKNGLFGNLIALSLGLTPNFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHI
ANLAGSPAIKKGILQTVKVVDELVKVMGRHKPENIVIEMARENQTTQKGQKNSRERMKRIEEGIKELGSQILKEHPVENTQLNEKLYLYLQNGRDMYV
DQELDINRLSDYDVDHIVPQSFLKDDSIDNKVLTRSDKNRGKSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHDAYLNAVVGTALIKKYPKLESEFVYGDYKVYDVRKMIAKSEQ
EIGKATAKYFFYSNIMNFFKTEITLANGEIRKRPLIETNGETGEIVWDKGRDFATVRKVLSMPQVNIVKKTEVQTGGFSKESILPKRNSDKLIARKKDWDPKK
YGGFDSPTVAYSVLVVAKVEKGKSKKLKSVKELLGITIMERSSFEKNPIDFLEAKGYKEVKKDLIIKLPKYSLFELENGRKRMLASAGELQKGNELALPSKYVNF
LYLASHYEKLKGSPEDNEQKQLFVEQHKHYLDEIIEQISEFSKRVILADANLDKVLSAYNKHRDKPIREQAENIIHLFTLTNLGAPAAFKYFDTTIDRKRYTSTK
EVLDATLIHQSITGLYETRIDLSQLGGD (SEQ ID NO:4)

FIG. 5

Sth1Cas9 (S. thermophilus) amino acid

MSDLVLGLDIGIGSVGVGILNKVTGEIIHKNSRIFPAAQAENNLVRRTNROGRRLARRKKHRRVRLNRLFEESGLITDFTKISINLNPYQLRVKGLTDELSNEE
LFIALKNMVKHRGISYLDDASDDGNSSVGDYAQIVKENSKQLETKTPGQIQLERYQTYGQLRGDFTVEKDGKKHRLINVFPTSAYRSEALRILQTQQEFNP
QITDEFINRYLEILTGKRKYYHGPGNEKSRTDYGRYRTSGETLDNIFGILIGKCTFYPDEFRAAKASYTAQEFNLLNDLNNLTVPTETKKLSKEQKNQIINYVKN
EKAMGPAKLFKYIAKLLSCDVADIKGYRIDKSGKAEIHTFEAYRKMKTLETLDIEQMDRETLDKLAYVLTLNTEREGIQEALEHEFADGSFSQKQVDELVQFR
KANSSIFGKGWHNFSVKLMMELIPELYETSEEQMTILTRLGKQKTTSSSNKTKYIDEKLLTEEIYNPVVAKSVRQAIKIVNAAIKEYGDFDNIVIEMARETNED
DEKKAIQKIQKANKDEKDAAMLKAANQYNGKAELPHSVFHGHKQLATKIRLWHQQGERCLYTGKTISIHDLINNSNQFEVDHILPLSITFDDSLANKVLVY
ATANQEKGQRTPYQALDSMDDAWSFRELKAFVRESKTLSNKKKEYLLTEEDISKFDVRKKFIERNLVDTRYASRVVLNALQEHFRAHKIDTKVSVVRGQFT
SQLRRHWGIEKTRDTYHHHAVDALIAASSQLNLWKKQKNTLVSYSEDQLLDIETGELISDDEYKESVFKAPYQHFVDTLKSKEFEDSILFSYQVDSKFNRKIS
DATIYATRQAKVGKDKADETYVLGKIDYTQDGYDAFMKIYKKDKSKFLMYRHDPQTFEKVIEPILENYPNKQINEKGKEVPCNPFLKYKEEHGYIRKYSKK
GNGPEIKSLKYYDSKLGNHIDITPKDSNNKVVLQSVSPWRADVYFNKTTGKYEILGLLKYADLQFEKGTGTYKISQEKYNDIKKKEGVDSDSEFKFTLYKNDLL
LVKDTETKEQQLFRFLSRTMPKQKHYVELKPYDKQKFEGGEALIKVLGNVANSGQCKKGLGKSNISIYKVRTDVLGNQHIIKNEGDKPKLDF (SEQ ID
NO:5)

FIG. 6

LgaCas9 (L. gasseri) amino acid

MTKIKNEYIVGLDIGTNSCGWVAMDFQNTILRMHGKTAIGSHLFDAGNSAADRRAFRTTRRRIKRKWRLKLLEEIFDPYMTEVDPYFFARLKESGLSPLD
KRKNASSIVFPTALEDKKFYCNYPTIYHLRYDLMSEDKKFDLREIYLAIHHIVKYRGNFLYNTPVKDFEASKIDVKDSLEKLNELYERLDSEFTVELDSSNALEIEK
IIRDKNVFKINKVKSIHQLLSLKTENKERTKLIKDVSKQIINAILGYKTKFETILLKNISKDEADDWEFKLTDVDADNKFENLIGDLNENEQEILLVIRNLANAITLS
NIVEEGKTLSESMIDKYNKHSDDLKLLKQVISDHPDRDKAKKLALAYDLYVNNRHGKLLQAKDVLGSKKTLSKEDFYKEVKKNLDDSKASQEILDAIALDSF
MPKQRTNENGVIPYQLHQLELDRIIKNQGKYYPFLKEANPVSSHLKQAPYKLDELIRFRVPYYVGPLISPNESTKNQTKKNQNFAWMIRKEQGQITPWN
FDQKVDRMASANKFIKRMTTKDTYLLGEDVLPANSLLYQKFTVLNELNNIKINGKRISVPLKQELYNNLFKKNSTVTTNKLKSYLKENYNLINVEIKGLADEK
KFNSGLTTYNKLRNLKIFDQQIDDLNYDKDFERIIEWSTIFEDKAIYKDKLKTIKWLSDRQIDKLSKIRMQGWGQLSKKLLSQLTDNNGQTIIEQLWDSQNN
FMQIVNQADFKDAIAVANQNLLVNTSVEDILNEAYTSPANKKAIRQVKVVVDDIVKAASGKVPKQJAIEFTRDADDKAKISQTRANKLRKVYKELSNELASE
AIRNELERVAKDQKLLKDKYYLFMQLGRDAYTGEPIDIDELEQYDIDHILPQSFIKDDSLENRVLVKKAVNNGKSDNVPVKLYGNHMAADLGITIRHMWE
KWKDQGLITKTKYNNLIIDPDKINKYESSGFIHRQLVETSQIIKLASTILQSKYPDTEIIVVKARYNHYLRKHLNLYKSREVNDYHHAIDAYLSAICGNLLYQVYP
YLRPFFVYGQYKKFSSDPKKEKIIYDKTRKYNFISQIFENKGNDIISLETKKKVFDKKDIIEKLKHAYDYKYMLVSRETETRDQEMFKMTVYPRLSRDTKKSRNLI
PKKKDMPTEIYGGYTNNSDAYMVIARINKKETEYRVFGVPMRELVNLRKAEKKGHYNAYLKQVLEPEIMYNKNGKNKTISSFEIVSKVPYKQVILDGD
KKFMLGSSTYVVNAKQLTLSQDAMQAITDNCENDTDEEKALIEAYDEILTNIDKYLPLFDINKFRDKLHAGREKFINLSLDVKKDTILQVLNGLHDNAVMPKI
KSLGLSTELGLKLQIPTGVKLSENAKLIYQSPTGLFEKRVKISDL (SEQ ID NO:6)

SEQUENCE LISTING

<160> NUMBER OF SEQ ID NOS: 50

<210> SEQ ID NO 1
<211> LENGTH: 187

```
<212> TYPE: PRT
<213> ORGANISM: Artificial Sequence
<220> FEATURE:
<223> OTHER INFORMATION: Synthetic sequence

<400> SEQUENCE: 1

Met Arg Glu Thr Ile Gln Arg Leu Leu Ala Ser Asn Leu Ser Ser Asn
 1               5                  10                  15

Ser Ile Ala Leu Ala Thr Gly Val Ser Gln Ala Val Ile Ser Lys Leu
            20                  25                  30

Arg Asn Ala Lys Lys Glu Ile Gly Asn Leu Ser Leu Asn Ser Ala Glu
        35                  40                  45

Lys Leu Tyr Asn Tyr Gln Lys Gly Leu Glu Val Met Asn Lys Ser Ile
    50                  55                  60

Glu Ile Lys Asp Gln Asn Asn Ile Val Leu Ile Asp Ser Leu Gly Gln
 65                 70                   75                  80

Phe Phe Thr Asp Ile Glu Asn Asp Asn Gly Arg Tyr Asn Ile Asp
            85                  90                  95

Tyr Val Leu Leu Asn Glu Val Glu His Asp Asn Gly Asn Thr Tyr Tyr
            100                 105                 110

Glu Val Gly Met Tyr Arg Thr Glu Glu Val Pro Phe Ser Asp Lys Val
            115                 120                 125

Thr Gln Asp Asn Val Glu Leu Leu Glu Asp Lys Trp Leu Gln Ile Asp
    130                 135                 140

Gln Gln Gly Glu Ser Tyr Val Glu Ser Ile Phe Phe Glu Asn Glu Glu
145                 150                 155                 160

Asp Ala Arg Glu Tyr Ile Lys Leu Val Leu Lys Gly His Glu Thr Phe
                165                 170                 175

Glu Glu Thr Ala Lys Ala Ile Gly Val Ile Lys
            180                 185

<210> SEQ ID NO 2
<211> LENGTH: 564
<212> TYPE: DNA
<213> ORGANISM: Artificial sequence
<220> FEATURE:
<223> OTHER INFORMATION: Synthetic sequence

<400> SEQUENCE: 2
atgagggaaa caattcaacg gctgctcgcg tctaacctca gtagcaattc aatcgctttg    60
gccacaggcg taagccaggc agttattagc aaactgcgga atgccaaaaa agagataggc   120
aacctttctc tcaatagcgc ggaaaagttg tataattacc agaagggcct ggaagtcatg   180
aacaaatcta tcgagatcaa agatcaaaac aacatagtcc tgattgacag tcttggacag   240
ttctttacag acatcgaaaa tgataataac ggtcgatata acatcgacta cgtgctgctc   300
aacgaggtag aacacgacaa tggcaacacg tactacgaag tgggcatgta tcggaccgaa   360
gaggtaccct tttccgacaa agtgacccag gacaatgtag aacttctgga ggataaatgg   420
ctgcaaatag atcaacaagg cgagagctat gttgaaagca tttttttga gaacgaagag   480 gacgctagag aatatattaa gttggtcctg aagggtcatg agacatttga ggaacggct    540 aaagcaatcg gagtcatcaa gtaa                                          564

<210> SEQ ID NO 3
<211> LENGTH: 1054
<212> TYPE: PRT
<213> ORGANISM: Staphylococcus aureus
```

```
<400> SEQUENCE: 3

Met Gly Lys Arg Asn Tyr Ile Leu Gly Leu Asp Ile Gly Ile Thr Ser
1               5                   10                  15

Val Gly Tyr Gly Ile Ile Asp Tyr Glu Thr Arg Asp Val Ile Asp Ala
            20                  25                  30

Gly Val Arg Leu Phe Lys Glu Ala Asn Val Glu Asn Asn Glu Gly Arg
        35                  40                  45

Arg Ser Lys Arg Gly Ala Arg Arg Leu Lys Arg Arg Arg Arg His Arg
    50                  55                  60

Ile Gln Arg Val Lys Lys Leu Leu Phe Asp Tyr Asn Leu Leu Thr Asp
65                  70                  75                  80

His Ser Glu Leu Ser Gly Ile Asn Pro Tyr Glu Ala Arg Val Lys Gly
                85                  90                  95

Leu Ser Gln Lys Leu Ser Glu Glu Phe Ser Ala Ala Leu Leu His
            100                 105                 110

Leu Ala Lys Arg Arg Gly Val His Asn Val Asn Glu Val Glu Glu Asp
            115                 120                 125

Thr Gly Asn Glu Leu Ser Thr Lys Glu Gln Ile Ser Arg Asn Ser Lys
    130                 135                 140

Ala Leu Glu Glu Lys Tyr Val Ala Glu Leu Gln Leu Glu Arg Leu Lys
145                 150                 155                 160

Lys Asp Gly Glu Val Arg Gly Ser Ile Asn Arg Phe Lys Thr Ser Asp
                165                 170                 175

Tyr Val Lys Glu Ala Lys Gln Leu Leu Lys Val Gln Lys Ala Tyr His
            180                 185                 190

Gln Leu Asp Gln Ser Phe Ile Asp Thr Tyr Ile Asp Leu Leu Glu Thr
        195                 200                 205

Arg Arg Thr Tyr Tyr Glu Gly Pro Gly Glu Gly Ser Pro Phe Gly Trp
    210                 215                 220

Lys Asp Ile Lys Glu Trp Tyr Glu Met Leu Met Gly His Cys Thr Tyr
225                 230                 235                 240

Phe Pro Glu Glu Leu Arg Ser Val Lys Tyr Ala Tyr Asn Ala Asp Leu
                245                 250                 255

Tyr Asn Ala Leu Asn Asp Leu Asn Asn Leu Val Ile Thr Arg Asp Glu
            260                 265                 270

Asn Glu Lys Leu Glu Tyr Tyr Glu Lys Phe Gln Ile Ile Glu Asn Val
        275                 280                 285

Phe Lys Gln Lys Lys Lys Pro Thr Leu Lys Gln Ile Ala Lys Glu Ile
    290                 295                 300

Leu Val Asn Glu Glu Asp Ile Lys Gly Tyr Arg Val Thr Ser Thr Gly
305                 310                 315                 320

Lys Pro Glu Phe Thr Asn Leu Lys Val Tyr His Asp Ile Lys Asp Ile
                325                 330                 335

Thr Ala Arg Lys Glu Ile Ile Glu Asn Ala Glu Leu Leu Asp Gln Ile
            340                 345                 350

Ala Lys Ile Leu Thr Ile Tyr Gln Ser Ser Glu Asp Ile Gln Glu Glu
        355                 360                 365

Leu Thr Asn Leu Asn Ser Glu Leu Thr Gln Glu Ile Glu Gln Ile
    370                 375                 380

Ser Asn Leu Lys Gly Tyr Thr Gly Thr His Asn Leu Ser Leu Lys Ala
385                 390                 395                 400

Ile Asn Leu Ile Leu Asp Glu Leu Trp His Thr Asn Asp Asn Gln Ile
                405                 410                 415
```

```
Ala Ile Phe Asn Arg Leu Lys Leu Val Pro Lys Lys Val Asp Leu Ser
            420                 425                 430

Gln Gln Lys Glu Ile Pro Thr Thr Leu Val Asp Asp Phe Ile Leu Ser
            435                 440                 445

Pro Val Val Lys Arg Ser Phe Ile Gln Ser Ile Lys Val Ile Asn Ala
            450                 455                 460

Ile Ile Lys Lys Tyr Gly Leu Pro Asn Asp Ile Ile Glu Leu Ala
465             470                 475                 480

Arg Glu Lys Asn Ser Lys Asp Ala Gln Lys Met Ile Asn Glu Met Gln
                485                 490                 495

Lys Arg Asn Arg Gln Thr Asn Glu Arg Ile Glu Glu Ile Ile Arg Thr
            500                 505                 510

Thr Gly Lys Glu Asn Ala Lys Tyr Leu Ile Glu Lys Ile Lys Leu His
            515                 520                 525

Asp Met Gln Glu Gly Lys Cys Leu Tyr Ser Leu Glu Ala Ile Pro Leu
            530                 535                 540

Glu Asp Leu Leu Asn Asn Pro Phe Asn Tyr Glu Val Asp His Ile Ile
545                 550                 555                 560

Pro Arg Ser Val Ser Phe Asp Asn Ser Phe Asn Asn Lys Val Leu Val
                565                 570                 575

Lys Gln Glu Glu Asn Ser Lys Lys Gly Asn Arg Thr Pro Phe Gln Tyr
            580                 585                 590

Leu Ser Ser Ser Asp Ser Lys Ile Ser Tyr Glu Thr Phe Lys Lys His
            595                 600                 605

Ile Leu Asn Leu Ala Lys Gly Lys Gly Arg Ile Ser Lys Thr Lys Lys
            610                 615                 620

Glu Tyr Leu Leu Glu Glu Arg Asp Ile Asn Arg Phe Ser Val Gln Lys
625                 630                 635                 640

Asp Phe Ile Asn Arg Asn Leu Val Asp Thr Arg Tyr Ala Thr Arg Gly
                645                 650                 655

Leu Met Asn Leu Leu Arg Ser Tyr Phe Arg Val Asn Asn Leu Asp Val
            660                 665                 670

Lys Val Lys Ser Ile Asn Gly Gly Phe Thr Ser Phe Leu Arg Arg Lys
            675                 680                 685

Trp Lys Phe Lys Lys Glu Arg Asn Lys Gly Tyr Lys His His Ala Glu
            690                 695                 700

Asp Ala Leu Ile Ile Ala Asn Ala Asp Phe Ile Phe Lys Glu Trp Lys
705                 710                 715                 720

Lys Leu Asp Lys Ala Lys Lys Val Met Glu Asn Gln Met Phe Glu Glu
                725                 730                 735

Lys Gln Ala Glu Ser Met Pro Glu Ile Glu Thr Glu Gln Glu Tyr Lys
            740                 745                 750

Glu Ile Phe Ile Thr Pro His Gln Ile Lys His Ile Lys Asp Phe Lys
            755                 760                 765

Asp Tyr Lys Tyr Ser His Arg Val Asp Lys Lys Pro Asn Arg Glu Leu
            770                 775                 780

Ile Asn Asp Thr Leu Tyr Ser Thr Arg Lys Asp Asp Lys Gly Asn Thr
785                 790                 795                 800

Leu Ile Val Asn Asn Leu Asn Gly Leu Tyr Asp Lys Asp Asn Asp Lys
                805                 810                 815

Leu Lys Lys Leu Ile Asn Lys Ser Pro Glu Lys Leu Leu Met Tyr His
            820                 825                 830
```

His Asp Pro Gln Thr Tyr Gln Lys Leu Lys Leu Ile Met Glu Gln Tyr
835                 840                 845

Gly Asp Glu Lys Asn Pro Leu Tyr Lys Tyr Glu Glu Thr Gly Asn
850                 855                 860

Tyr Leu Thr Lys Tyr Ser Lys Lys Asp Asn Gly Pro Val Ile Lys Lys
865                 870                 875                 880

Ile Lys Tyr Tyr Gly Asn Lys Leu Asn Ala His Leu Asp Ile Thr Asp
                885                 890                 895

Asp Tyr Pro Asn Ser Arg Asn Lys Val Lys Leu Ser Leu Lys Pro
            900                 905                 910

Tyr Arg Phe Asp Val Tyr Leu Asp Asn Gly Val Tyr Lys Phe Val Thr
        915                 920                 925

Val Lys Asn Leu Asp Val Ile Lys Lys Glu Asn Tyr Tyr Glu Val Asn
    930                 935                 940

Ser Lys Cys Tyr Glu Glu Ala Lys Lys Leu Lys Lys Ile Ser Asn Gln
945                 950                 955                 960

Ala Glu Phe Ile Ala Ser Phe Tyr Asn Asn Asp Leu Ile Lys Ile Asn
                965                 970                 975

Gly Glu Leu Tyr Arg Val Ile Gly Val Asn Asn Asp Leu Leu Asn Arg
            980                 985                 990

Ile Glu Val Asn Met Ile Asp Ile Thr Tyr Arg Glu Tyr Leu Glu Asn
        995                 1000                1005

Met Asn Asp Lys Arg Pro Pro Arg Ile Ile Lys Thr Ile Ala Ser
        1010                1015                1020

Lys Thr Gln Ser Ile Lys Lys Tyr Ser Thr Asp Ile Leu Gly Asn
        1025                1030                1035

Leu Tyr Glu Val Lys Ser Lys Lys His Pro Gln Ile Ile Lys Lys
        1040                1045                1050

Gly

<210> SEQ ID NO 4
<211> LENGTH: 1368
<212> TYPE: PRT
<213> ORGANISM: Streptococcus pyogenes

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
```

```
                565                 570                 575
Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990
```

```
Val Gly Thr Ala Leu Ile Lys Lys  Tyr Pro Lys Leu Glu  Ser Glu Phe
        995                 1000               1005

Val Tyr  Gly Asp Tyr Lys Val  Tyr Asp Val Arg  Lys Met Ile Ala
    1010                 1015               1020

Lys Ser  Glu Gln Glu Ile Gly  Lys Ala Thr Ala  Lys Tyr Phe Phe
    1025                 1030               1035

Tyr Ser  Asn Ile Met Asn Phe  Phe Lys Thr Glu  Ile Thr Leu Ala
    1040                 1045               1050

Asn Gly  Glu Ile Arg Lys Arg  Pro Leu Ile Glu  Thr Asn Gly Glu
    1055                 1060               1065

Thr Gly  Glu Ile Val Trp Asp  Lys Gly Arg Asp  Phe Ala Thr Val
    1070                 1075               1080

Arg Lys  Val Leu Ser Met Pro  Gln Val Asn Ile  Val Lys Lys Thr
    1085                 1090               1095

Glu Val  Gln Thr Gly Gly Phe  Ser Lys Glu Ser  Ile Leu Pro Lys
    1100                 1105               1110

Arg Asn  Ser Asp Lys Leu Ile  Ala Arg Lys Lys  Asp Trp Asp Pro
    1115                 1120               1125

Lys Lys  Tyr Gly Gly Phe Asp  Ser Pro Thr Val  Ala Tyr Ser Val
    1130                 1135               1140

Leu Val  Val Ala Lys Val Glu  Lys Gly Lys Ser  Lys Lys Leu Lys
    1145                 1150               1155

Ser Val  Lys Glu Leu Leu Gly  Ile Thr Ile Met  Glu Arg Ser Ser
    1160                 1165               1170

Phe Glu  Lys Asn Pro Ile Asp  Phe Leu Glu Ala  Lys Gly Tyr Lys
    1175                 1180               1185

Glu Val  Lys Lys Asp Leu Ile  Ile Lys Leu Pro  Lys Tyr Ser Leu
    1190                 1195               1200

Phe Glu  Leu Glu Asn Gly Arg  Lys Arg Met Leu Ala  Ser Ala Gly
    1205                 1210               1215

Glu Leu  Gln Lys Gly Asn Glu  Leu Ala Leu Pro  Ser Lys Tyr Val
    1220                 1225               1230

Asn Phe  Leu Tyr Leu Ala Ser  His Tyr Glu Lys  Leu Lys Gly Ser
    1235                 1240               1245

Pro Glu  Asp Asn Glu Gln Lys  Gln Leu Phe Val  Glu Gln His Lys
    1250                 1255               1260

His Tyr  Leu Asp Glu Ile Ile  Glu Gln Ile Ser  Glu Phe Ser Lys
    1265                 1270               1275

Arg Val  Ile Leu Ala Asp Ala  Asn Leu Asp Lys  Val Leu Ser Ala
    1280                 1285               1290

Tyr Asn  Lys His Arg Asp Lys  Pro Ile Arg Glu  Gln Ala Glu Asn
    1295                 1300               1305

Ile Ile  His Leu Phe Thr Leu  Thr Asn Leu Gly  Ala Pro Ala Ala
    1310                 1315               1320

Phe Lys  Tyr Phe Asp Thr Thr  Ile Asp Arg Lys  Arg Tyr Thr Ser
    1325                 1330               1335

Thr Lys  Glu Val Leu Asp Ala  Thr Leu Ile His  Gln Ser Ile Thr
    1340                 1345               1350

Gly Leu  Tyr Glu Thr Arg Ile  Asp Leu Ser Gln  Leu Gly Gly Asp
    1355                 1360               1365

<210> SEQ ID NO 5
<211> LENGTH: 1121
```

```
<212> TYPE: PRT
<213> ORGANISM: Streptococcus thermophilus

<400> SEQUENCE: 5

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Gly
        115                 120                 125

Asn Ser Ser Val Gly Asp Tyr Ala Gln Ile Val Lys Glu Asn Ser Lys
130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400
```

-continued

```
Phe Ser Gln Lys Gln Val Asp Glu Leu Val Gln Phe Arg Lys Ala Asn
            405                 410                 415
Ser Ser Ile Phe Gly Lys Gly Trp His Asn Phe Ser Val Lys Leu Met
        420                 425                 430
Met Glu Leu Ile Pro Glu Leu Tyr Glu Thr Ser Glu Glu Gln Met Thr
            435                 440                 445
Ile Leu Thr Arg Leu Gly Lys Gln Lys Thr Thr Ser Ser Asn Lys
450                 455                 460
Thr Lys Tyr Ile Asp Glu Lys Leu Leu Thr Glu Ile Tyr Asn Pro
465                 470                 475             480
Val Val Ala Lys Ser Val Arg Gln Ala Ile Lys Ile Val Asn Ala Ala
            485                 490                 495
Ile Lys Glu Tyr Gly Asp Phe Asp Asn Ile Val Ile Glu Met Ala Arg
            500                 505                 510
Glu Thr Asn Glu Asp Asp Glu Lys Lys Ala Ile Gln Lys Ile Gln Lys
            515                 520                 525
Ala Asn Lys Asp Glu Lys Asp Ala Ala Met Leu Lys Ala Ala Asn Gln
            530                 535                 540
Tyr Asn Gly Lys Ala Glu Leu Pro His Ser Val Phe His Gly His Lys
545                 550                 555                 560
Gln Leu Ala Thr Lys Ile Arg Leu Trp His Gln Gln Gly Glu Arg Cys
            565                 570                 575
Leu Tyr Thr Gly Lys Thr Ile Ser Ile His Asp Leu Ile Asn Asn Ser
            580                 585                 590
Asn Gln Phe Glu Val Asp His Ile Leu Pro Leu Ser Ile Thr Phe Asp
            595                 600                 605
Asp Ser Leu Ala Asn Lys Val Leu Val Tyr Ala Thr Ala Asn Gln Glu
610                 615                 620
Lys Gly Gln Arg Thr Pro Tyr Gln Ala Leu Asp Ser Met Asp Asp Ala
625                 630                 635             640
Trp Ser Phe Arg Glu Leu Lys Ala Phe Val Arg Glu Ser Lys Thr Leu
            645                 650                 655
Ser Asn Lys Lys Lys Glu Tyr Leu Leu Thr Glu Glu Asp Ile Ser Lys
            660                 665                 670
Phe Asp Val Arg Lys Lys Phe Ile Glu Arg Asn Leu Val Asp Thr Arg
            675                 680                 685
Tyr Ala Ser Arg Val Val Leu Asn Ala Leu Gln Glu His Phe Arg Ala
            690                 695                 700
His Lys Ile Asp Thr Lys Val Ser Val Val Arg Gly Gln Phe Thr Ser
705                 710                 715                 720
Gln Leu Arg Arg His Trp Gly Ile Glu Lys Thr Arg Asp Thr Tyr His
            725                 730                 735
His His Ala Val Asp Ala Leu Ile Ile Ala Ala Ser Ser Gln Leu Asn
            740                 745                 750
Leu Trp Lys Lys Gln Lys Asn Thr Leu Val Ser Tyr Ser Glu Asp Gln
            755                 760                 765
Leu Leu Asp Ile Glu Thr Gly Glu Leu Ile Ser Asp Asp Glu Tyr Lys
            770                 775                 780
Glu Ser Val Phe Lys Ala Pro Tyr Gln His Phe Val Asp Thr Leu Lys
785                 790                 795             800
Ser Lys Glu Phe Glu Asp Ser Ile Leu Phe Ser Tyr Gln Val Asp Ser
            805                 810                 815
```

```
Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
            835                 840                 845

Ile Lys Asp Ile Tyr Thr Gln Asp Gly Tyr Asp Ala Phe Met Lys Ile
        850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser Gln Glu Lys Tyr Asn Asp Ile Lys
        995                 1000                1005

Lys Lys Glu Gly Val Asp Ser Asp Ser Glu Phe Lys Phe Thr Leu
    1010                1015                1020

Tyr Lys Asn Asp Leu Leu Leu Val Lys Asp Thr Glu Thr Lys Glu
    1025                1030                1035

Gln Gln Leu Phe Arg Phe Leu Ser Arg Thr Met Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Ser Gly
    1070                1075                1080

Gln Cys Lys Lys Gly Leu Gly Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120

<210> SEQ ID NO 6
<211> LENGTH: 1386
<212> TYPE: PRT
<213> ORGANISM: Lactobacillus gasseri

<400> SEQUENCE: 6

Met Thr Lys Ile Lys Asn Glu Tyr Ile Val Gly Leu Asp Ile Gly Thr
1               5                   10                  15

Asn Ser Cys Gly Trp Val Ala Met Asp Phe Gln Asn Thr Ile Leu Arg
            20                  25                  30

Met His Gly Lys Thr Ala Ile Gly Ser His Leu Phe Asp Ala Gly Asn
        35                  40                  45

Ser Ala Ala Asp Arg Arg Ala Phe Arg Thr Thr Arg Arg Arg Ile Lys
    50                  55                  60
```

```
Arg Arg Lys Trp Arg Leu Lys Leu Leu Glu Glu Ile Phe Asp Pro Tyr
 65                  70                  75                  80

Met Thr Glu Val Asp Pro Tyr Phe Phe Ala Arg Leu Lys Glu Ser Gly
                 85                  90                  95

Leu Ser Pro Leu Asp Lys Arg Lys Asn Ala Ser Ser Ile Val Phe Pro
            100                 105                 110

Thr Ala Leu Glu Asp Lys Lys Phe Tyr Cys Asn Tyr Pro Thr Ile Tyr
            115                 120                 125

His Leu Arg Tyr Asp Leu Met Ser Glu Asp Lys Lys Phe Asp Leu Arg
130             135                 140

Glu Ile Tyr Leu Ala Ile His His Ile Val Lys Tyr Arg Gly Asn Phe
145             150                 155                 160

Leu Tyr Asn Thr Pro Val Lys Asp Phe Glu Ala Ser Lys Ile Asp Val
            165                 170                 175

Lys Asp Ser Leu Glu Lys Leu Asn Glu Leu Tyr Glu Arg Leu Asp Ser
            180                 185                 190

Glu Phe Thr Val Glu Leu Asp Ser Ser Asn Ala Leu Glu Ile Glu Lys
            195                 200                 205

Ile Ile Arg Asp Lys Asn Val Phe Lys Ile Asn Lys Val Lys Ser Ile
            210                 215                 220

His Gln Leu Leu Ser Leu Lys Thr Glu Asn Lys Glu Arg Thr Lys Leu
225             230                 235                 240

Ile Lys Asp Val Ser Lys Gln Ile Ile Asn Ala Ile Leu Gly Tyr Lys
            245                 250                 255

Thr Lys Phe Glu Thr Ile Leu Leu Lys Asn Ile Ser Lys Asp Glu Ala
            260                 265                 270

Asp Asp Trp Glu Phe Lys Leu Thr Asp Val Asp Ala Asp Asn Lys Phe
            275                 280                 285

Glu Asn Leu Ile Gly Asp Leu Asn Glu Asn Glu Gln Glu Ile Leu Leu
            290                 295                 300

Val Ile Arg Asn Leu Ala Asn Ala Ile Thr Leu Ser Asn Ile Val Glu
305             310                 315                 320

Glu Gly Lys Thr Leu Ser Glu Ser Met Ile Asp Lys Tyr Asn Lys His
            325                 330                 335

Ser Asp Asp Leu Lys Leu Leu Lys Gln Val Ile Ser Asp His Pro Asp
            340                 345                 350

Arg Asp Lys Ala Lys Lys Leu Ala Leu Ala Tyr Asp Leu Tyr Val Asn
            355                 360                 365

Asn Arg His Gly Lys Leu Leu Gln Ala Lys Asp Val Leu Gly Ser Lys
            370                 375                 380

Lys Thr Leu Ser Lys Glu Asp Phe Tyr Lys Glu Val Leu Lys Asn Leu
385             390                 395                 400

Asp Asp Ser Lys Ala Ser Gln Glu Ile Leu Asp Ala Ile Ala Leu Asp
            405                 410                 415

Ser Phe Met Pro Lys Gln Arg Thr Asn Glu Asn Gly Val Ile Pro Tyr
            420                 425                 430

Gln Leu His Gln Leu Glu Leu Asp Arg Ile Ile Lys Asn Gln Gly Lys
            435                 440                 445

Tyr Tyr Pro Phe Leu Lys Glu Ala Asn Pro Val Ser Ser His Leu Lys
            450                 455                 460

Gln Ala Pro Tyr Lys Leu Asp Glu Leu Ile Arg Phe Arg Val Pro Tyr
465             470                 475                 480
```

```
Tyr Val Gly Pro Leu Ile Ser Pro Asn Glu Ser Thr Lys Asn Lys Gln
                485                 490                 495

Thr Lys Lys Asn Gln Asn Phe Ala Trp Met Ile Arg Lys Glu Gln Gly
            500                 505                 510

Gln Ile Thr Pro Trp Asn Phe Asp Gln Lys Val Asp Arg Met Ala Ser
        515                 520                 525

Ala Asn Lys Phe Ile Lys Arg Met Thr Thr Lys Asp Thr Tyr Leu Leu
    530                 535                 540

Gly Glu Asp Val Leu Pro Ala Asn Ser Leu Leu Tyr Gln Lys Phe Thr
545                 550                 555                 560

Val Leu Asn Glu Leu Asn Asn Ile Lys Ile Asn Gly Lys Arg Ile Ser
                565                 570                 575

Val Pro Leu Lys Gln Glu Leu Tyr Asn Asn Leu Phe Lys Lys Asn Ser
            580                 585                 590

Thr Val Thr Thr Asn Lys Leu Lys Ser Tyr Leu Lys Glu Asn Tyr Asn
        595                 600                 605

Leu Ile Asn Val Glu Ile Lys Gly Leu Ala Asp Glu Lys Lys Phe Asn
    610                 615                 620

Ser Gly Leu Thr Thr Tyr Asn Lys Leu Arg Asn Leu Lys Ile Phe Asp
625                 630                 635                 640

Gln Gln Ile Asp Asp Leu Asn Tyr Asp Lys Asp Phe Glu Arg Ile Ile
                645                 650                 655

Glu Trp Ser Thr Ile Phe Glu Asp Lys Ala Ile Tyr Lys Asp Lys Leu
            660                 665                 670

Lys Thr Ile Lys Trp Leu Ser Asp Arg Gln Ile Asp Lys Leu Ser Lys
        675                 680                 685

Ile Arg Met Gln Gly Trp Gly Gln Leu Ser Lys Lys Leu Leu Ser Gln
    690                 695                 700

Leu Thr Asp Asn Asn Gly Gln Thr Ile Ile Glu Gln Leu Trp Asp Ser
705                 710                 715                 720

Gln Asn Asn Phe Met Gln Ile Val Asn Gln Ala Asp Phe Lys Asp Ala
                725                 730                 735

Ile Ala Val Ala Asn Gln Asn Leu Leu Val Asn Thr Ser Val Glu Asp
            740                 745                 750

Ile Leu Asn Glu Ala Tyr Thr Ser Pro Ala Asn Lys Lys Ala Ile Arg
        755                 760                 765

Gln Val Val Lys Val Val Asp Asp Ile Val Lys Ala Ala Ser Gly Lys
    770                 775                 780

Val Pro Lys Gln Ile Ala Ile Glu Phe Thr Arg Asp Ala Asp Asp Lys
785                 790                 795                 800

Ala Lys Ile Ser Gln Thr Arg Ala Asn Lys Leu Arg Lys Val Tyr Lys
                805                 810                 815

Glu Leu Ser Asn Glu Leu Ala Ser Glu Ala Ile Arg Asn Glu Leu Glu
            820                 825                 830

Arg Val Ala Lys Asp Gln Lys Leu Leu Lys Asp Lys Tyr Tyr Leu Tyr
        835                 840                 845

Phe Met Gln Leu Gly Arg Asp Ala Tyr Thr Gly Glu Pro Ile Asp Ile
    850                 855                 860

Asp Glu Leu Glu Gln Tyr Asp Ile Asp His Ile Leu Pro Gln Ser Phe
865                 870                 875                 880

Ile Lys Asp Asp Ser Leu Glu Asn Arg Val Leu Val Lys Lys Ala Val
                885                 890                 895

Asn Asn Gly Lys Ser Asp Asn Val Pro Val Lys Leu Tyr Gly Asn His
```

```
              900                 905                 910
Met Ala Ala Asp Leu Gly Ile Thr Ile Arg His Met Trp Glu Lys Trp
          915                 920                 925
Lys Asp Gln Gly Leu Ile Thr Lys Thr Lys Tyr Asn Asn Leu Ile Ile
          930                 935                 940
Asp Pro Asp Lys Ile Asn Lys Tyr Glu Ser Ser Gly Phe Ile His Arg
945                 950                 955                 960
Gln Leu Val Glu Thr Ser Gln Ile Ile Lys Leu Ala Ser Thr Ile Leu
              965                 970                 975
Gln Ser Lys Tyr Pro Asp Thr Glu Ile Ile Val Val Lys Ala Arg Tyr
          980                 985                 990
Asn His Tyr Leu Arg Lys His Leu Asn Leu Tyr Lys Ser Arg Glu Val
          995                1000                1005
Asn Asp Tyr His His Ala Ile Asp Ala Tyr Leu Ser Ala Ile Cys
        1010                1015                1020
Gly Asn Leu Leu Tyr Gln Val Tyr Pro Tyr Leu Arg Pro Phe Phe
        1025                1030                1035
Val Tyr Gly Gln Tyr Lys Lys Phe Ser Ser Asp Pro Lys Lys Glu
        1040                1045                1050
Lys Ile Ile Tyr Asp Lys Thr Arg Lys Tyr Asn Phe Ile Ser Gln
        1055                1060                1065
Ile Phe Glu Asn Lys Gly Asn Asp Ile Ile Ser Leu Glu Thr Lys
        1070                1075                1080
Lys Lys Val Phe Asp Lys Lys Asp Ile Ile Glu Lys Leu Lys His
        1085                1090                1095
Ala Tyr Asp Tyr Lys Tyr Met Leu Val Ser Arg Glu Thr Glu Thr
        1100                1105                1110
Arg Asp Gln Glu Met Phe Lys Met Thr Val Tyr Pro Arg Leu Ser
        1115                1120                1125
Arg Asp Thr Lys Lys Ser Arg Asn Leu Ile Pro Lys Lys Lys Asp
        1130                1135                1140
Met Pro Thr Glu Ile Tyr Gly Gly Tyr Thr Asn Asn Ser Asp Ala
        1145                1150                1155
Tyr Met Val Ile Ala Arg Ile Asn Lys Lys Lys Glu Thr Glu Tyr
        1160                1165                1170
Arg Val Phe Gly Val Pro Met Arg Glu Leu Val Asn Leu Arg Lys
        1175                1180                1185
Ala Glu Lys Lys Gly His Tyr Asn Ala Tyr Leu Lys Gln Val Leu
        1190                1195                1200
Glu Pro Glu Ile Met Tyr Asn Lys Asn Gly Lys Lys Asn Lys Thr
        1205                1210                1215
Ile Ser Ser Phe Glu Ile Val Lys Ser Lys Val Pro Tyr Lys Gln
        1220                1225                1230
Val Ile Leu Asp Gly Asp Lys Lys Phe Met Leu Gly Ser Ser Thr
        1235                1240                1245
Tyr Val Tyr Asn Ala Lys Gln Leu Thr Leu Ser Gln Asp Ala Met
        1250                1255                1260
Gln Ala Ile Thr Asp Asn Cys Glu Asn Asp Thr Asp Glu Glu Lys
        1265                1270                1275
Ala Leu Ile Glu Ala Tyr Asp Glu Ile Leu Thr Asn Ile Asp Lys
        1280                1285                1290
Tyr Leu Pro Leu Phe Asp Ile Asn Lys Phe Arg Asp Lys Leu His
        1295                1300                1305
```

Ala Gly Arg Glu Lys Phe Ile Asn Leu Ser Leu Asp Val Lys Lys
    1310                1315                1320

Asp Thr Ile Leu Gln Val Leu Asn Gly Leu His Asp Asn Ala Val
    1325                1330                1335

Met Pro Lys Ile Lys Ser Leu Gly Leu Ser Thr Glu Leu Gly Lys
    1340                1345                1350

Leu Gln Ile Pro Thr Gly Val Lys Leu Ser Glu Asn Ala Lys Leu
    1355                1360                1365

Ile Tyr Gln Ser Pro Thr Gly Leu Phe Glu Lys Arg Val Lys Ile
    1370                1375                1380

Ser Asp Leu
    1385

<210> SEQ ID NO 7
<211> LENGTH: 120
<212> TYPE: DNA
<213> ORGANISM: Artificial sequence
<220> FEATURE:
<223> OTHER INFORMATION: Synthetic sequence

<400> SEQUENCE: 7
gccttcgggc atggcggact tgttttttgta ctctcaagat tcaataatct tgcagaagct    60
acaaagataa ggcttcatgc cgaaatcaac accctgtcat tttatggcag ggtgttttcg   120

<210> SEQ ID NO 8
<211> LENGTH: 103
<212> TYPE: DNA
<213> ORGANISM: Artificial sequence
<220> FEATURE:
<223> OTHER INFORMATION: Synthetic sequence

<400> SEQUENCE: 8
gcaagggcga ggagctgttc acgtttttagt actctggaaa cagaatctac taaaacaagg    60
caaaatgccg tgtttatctc gtcaacttgt tggcgagatt ttt                      103

<210> SEQ ID NO 9
<211> LENGTH: 118
<212> TYPE: DNA
<213> ORGANISM: Artificial sequence
<220> FEATURE:
<223> OTHER INFORMATION: Synthetic sequence

<400> SEQUENCE: 9
ggtcgagctg gacggcgacg ttttagatgg ttgttaggaa actaacaacc agatttaaaa    60
tcaagcaatg catcttttga tgcaaagttt caatacttgt cccgagctat cgagggac     118

<210> SEQ ID NO 10
<211> LENGTH: 35
<212> TYPE: DNA
<213> ORGANISM: Artificial sequence
<220> FEATURE:
<223> OTHER INFORMATION: Synthetic sequence

<400> SEQUENCE: 10
ctgaagttca tctgcaccac gttttagagc tatct                                35

<210> SEQ ID NO 11
<211> LENGTH: 59
<212> TYPE: PRT
<213> ORGANISM: Artificial sequence
<220> FEATURE:

<223> OTHER INFORMATION: Synthetic sequence

<400> SEQUENCE: 11

Met Arg Glu Thr Ile Gln Arg Leu Leu Ala Ser Asn Leu Ser Ser Asn
1               5                   10                  15

Ser Ile Ala Leu Ala Thr Gly Val Ser Gln Ala Val Ile Ser Lys Leu
            20                  25                  30

Arg Asn Ala Lys Lys Glu Ile Gly Asn Leu Ser Leu Asn Ser Ala Glu
        35                  40                  45

Lys Leu Tyr Asn Tyr Gln Lys Gly Leu Glu Val
    50                  55

<210> SEQ ID NO 12
<211> LENGTH: 128
<212> TYPE: PRT
<213> ORGANISM: Artificial sequence
<220> FEATURE:
<223> OTHER INFORMATION: Synthetic sequence

<400> SEQUENCE: 12

Met Asn Lys Ser Ile Glu Ile Lys Asp Gln Asn Asn Ile Val Leu Ile
1               5                   10                  15

Asp Ser Leu Gly Gln Phe Phe Thr Asp Ile Glu Asn Asp Asn Asn Gly
            20                  25                  30

Arg Tyr Asn Ile Asp Tyr Val Leu Leu Asn Glu Val Glu His Asp Asn
        35                  40                  45

Gly Asn Thr Tyr Tyr Glu Val Gly Met Tyr Arg Thr Glu Glu Val Pro
    50                  55                  60

Phe Ser Asp Lys Val Thr Gln Asp Asn Val Glu Leu Leu Glu Asp Lys
65                  70                  75                  80

Trp Leu Gln Ile Asp Gln Gln Gly Glu Ser Tyr Val Glu Ser Ile Phe
                85                  90                  95

Phe Glu Asn Glu Glu Asp Ala Arg Glu Tyr Ile Lys Leu Val Leu Lys
            100                 105                 110

Gly His Glu Thr Phe Glu Glu Thr Ala Lys Ala Ile Gly Val Ile Lys
        115                 120                 125

<210> SEQ ID NO 13
<211> LENGTH: 16
<212> TYPE: PRT
<213> ORGANISM: Artificial sequence
<220> FEATURE:
<223> OTHER INFORMATION: Synthetic sequence

<400> SEQUENCE: 13

Lys Arg Pro Ala Ala Thr Lys Lys Ala Gly Gln Ala Lys Lys Lys Lys
1               5                   10                  15

<210> SEQ ID NO 14
<211> LENGTH: 9
<212> TYPE: PRT
<213> ORGANISM: Artificial sequence
<220> FEATURE:
<223> OTHER INFORMATION: Synthetic sequence

<400> SEQUENCE: 14

Pro Ala Ala Lys Arg Val Lys Leu Asp
1               5

<210> SEQ ID NO 15
<211> LENGTH: 11

```
<212> TYPE: PRT
<213> ORGANISM: Artificial sequence
<220> FEATURE:
<223> OTHER INFORMATION: Synthetic sequence

<400> SEQUENCE: 15

Arg Gln Arg Arg Asn Glu Leu Lys Arg Ser Pro
1               5                   10

<210> SEQ ID NO 16
<211> LENGTH: 38
<212> TYPE: PRT
<213> ORGANISM: Artificial sequence
<220> FEATURE:
<223> OTHER INFORMATION: Synthetic sequence

<400> SEQUENCE: 16

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 17
<211> LENGTH: 42
<212> TYPE: PRT
<213> ORGANISM: Artificial sequence
<220> FEATURE:
<223> OTHER INFORMATION: Synthetic sequence

<400> SEQUENCE: 17

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 18
<211> LENGTH: 8
<212> TYPE: PRT
<213> ORGANISM: Artificial sequence
<220> FEATURE:
<223> OTHER INFORMATION: Synthetic sequence

<400> SEQUENCE: 18

Val Ser Arg Lys Arg Pro Arg Pro
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic sequence

<400> SEQUENCE: 19

Pro Pro Lys Lys Ala Arg Glu Asp
1               5

<210> SEQ ID NO 20
<211> LENGTH: 8
<212> TYPE: PRT
<213> ORGANISM: Artificial sequence
```

```
<220> FEATURE:
<223> OTHER INFORMATION: Synthetic sequence

<400> SEQUENCE: 20

Pro Gln Pro Lys Lys Lys Pro Leu
1               5

<210> SEQ ID NO 21
<211> LENGTH: 12
<212> TYPE: PRT
<213> ORGANISM: Artificial sequence
<220> FEATURE:
<223> OTHER INFORMATION: Synthetic sequence

<400> SEQUENCE: 21

Ser Ala Leu Ile Lys Lys Lys Lys Lys Met Ala Pro
1               5                   10

<210> SEQ ID NO 22
<211> LENGTH: 5
<212> TYPE: PRT
<213> ORGANISM: Artificial sequence
<220> FEATURE:
<223> OTHER INFORMATION: Synthetic sequence

<400> SEQUENCE: 22

Asp Arg Leu Arg Arg
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic sequence

<400> SEQUENCE: 23

Pro Lys Gln Lys Lys Arg Lys
1               5

<210> SEQ ID NO 24
<211> LENGTH: 10
<212> TYPE: PRT
<213> ORGANISM: Artificial sequence
<220> FEATURE:
<223> OTHER INFORMATION: Synthetic sequence

<400> SEQUENCE: 24

Arg Lys Leu Lys Lys Lys Ile Lys Lys Leu
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic sequence

<400> SEQUENCE: 25

Arg Glu Lys Lys Lys Phe Leu Lys Arg Arg
1               5                   10

<210> SEQ ID NO 26
<211> LENGTH: 20
<212> TYPE: PRT
<213> ORGANISM: Artificial sequence
<220> FEATURE:
```

<223> OTHER INFORMATION: Synthetic sequence

<400> SEQUENCE: 26

Lys Arg Lys Gly Asp Glu Val Asp Gly Val Asp Glu Val Ala Lys Lys
1               5                   10                  15

Lys Ser Lys Lys
            20

<210> SEQ ID NO 27
<211> LENGTH: 17
<212> TYPE: PRT
<213> ORGANISM: Artificial sequence
<220> FEATURE:
<223> OTHER INFORMATION: Synthetic sequence

<400> SEQUENCE: 27

Arg Lys Cys Leu Gln Ala Gly Met Asn Leu Glu Ala Arg Lys Thr Lys
1               5                   10                  15

Lys

<210> SEQ ID NO 28
<211> LENGTH: 12
<212> TYPE: PRT
<213> ORGANISM: Artificial sequence
<220> FEATURE:
<223> OTHER INFORMATION: Synthetic sequence

<400> SEQUENCE: 28

Arg Arg Gln Arg Arg Thr Ser Lys Leu Met Lys Arg
1               5                   10

<210> SEQ ID NO 29
<211> LENGTH: 27
<212> TYPE: PRT
<213> ORGANISM: Artificial sequence
<220> FEATURE:
<223> OTHER INFORMATION: Synthetic sequence

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 30
<211> LENGTH: 33
<212> TYPE: PRT
<213> ORGANISM: Artificial sequence
<220> FEATURE:
<223> OTHER INFORMATION: Synthetic sequence

<400> SEQUENCE: 30

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 31
<211> LENGTH: 16
<212> TYPE: PRT
<213> ORGANISM: Artificial sequence
<220> FEATURE:
<223> OTHER INFORMATION: Synthetic sequence

<400> SEQUENCE: 31

Arg Gln Ile Lys Ile Trp Phe Gln Asn Arg Arg Met Lys Trp Lys Lys
1               5                   10                  15

<210> SEQ ID NO 32
<211> LENGTH: 11
<212> TYPE: PRT
<213> ORGANISM: Artificial sequence
<220> FEATURE:
<223> OTHER INFORMATION: Synthetic sequence

<400> SEQUENCE: 32

Tyr Gly Arg Lys Lys Arg Arg Gln Arg Arg Arg
1               5                   10

<210> SEQ ID NO 33
<211> LENGTH: 9
<212> TYPE: PRT
<213> ORGANISM: Artificial sequence
<220> FEATURE:
<223> OTHER INFORMATION: Synthetic sequence

<400> SEQUENCE: 33

Arg Lys Lys Arg Arg Gln Arg Arg Arg
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic sequence

<400> SEQUENCE: 34

Arg Lys Lys Arg Arg Gln Arg Arg
1               5

<210> SEQ ID NO 35
<211> LENGTH: 11
<212> TYPE: PRT
<213> ORGANISM: Artificial sequence
<220> FEATURE:
<223> OTHER INFORMATION: Synthetic sequence

<400> SEQUENCE: 35

Tyr Ala Arg Ala Ala Ala Arg Gln Ala Arg Ala
1               5                   10

<210> SEQ ID NO 36
<211> LENGTH: 11
<212> TYPE: PRT
<213> ORGANISM: Artificial sequence
<220> FEATURE:
<223> OTHER INFORMATION: Synthetic sequence

<400> SEQUENCE: 36

Thr His Arg Leu Pro Arg Arg Arg Arg Arg Arg
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic sequence

```
<400> SEQUENCE: 37

Gly Gly Arg Arg Ala Arg Arg Arg Arg Arg
1               5                   10

<210> SEQ ID NO 38
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (5)..(5)
<223> OTHER INFORMATION: this amino acid residue may be repeated

<400> SEQUENCE: 38

Gly Ser Gly Gly Ser
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (6)..(6)
<223> OTHER INFORMATION: This amino acid residue may be repeated

<400> SEQUENCE: 39

Gly Gly Ser Gly Gly Ser
1               5

<210> SEQ ID NO 40
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (5)..(5)
<223> OTHER INFORMATION: This amino acid residue may be repeated

<400> SEQUENCE: 40

Gly Gly Gly Gly Ser
1               5

<210> SEQ ID NO 41
<211> LENGTH: 4
<212> TYPE: PRT
<213> ORGANISM: Artificial sequence
<220> FEATURE:
<223> OTHER INFORMATION: Synthetic sequence

<400> SEQUENCE: 41

Gly Gly Ser Gly
1

<210> SEQ ID NO 42
<211> LENGTH: 5
<212> TYPE: PRT
<213> ORGANISM: Artificial sequence
<220> FEATURE:
<223> OTHER INFORMATION: Synthetic sequence

<400> SEQUENCE: 42
```

```
<210> SEQ ID NO 43
<211> LENGTH: 5
<212> TYPE: PRT
<213> ORGANISM: Artificial sequence
<220> FEATURE:
<223> OTHER INFORMATION: Synthetic sequence

<400> SEQUENCE: 43

Gly Ser Gly Ser Gly
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic sequence

<400> SEQUENCE: 44

Gly Ser Gly Gly Gly
1               5

<210> SEQ ID NO 45
<211> LENGTH: 5
<212> TYPE: PRT
<213> ORGANISM: Artificial sequence
<220> FEATURE:
<223> OTHER INFORMATION: Synthetic sequence

<400> SEQUENCE: 45

Gly Gly Gly Ser Gly
1               5

<210> SEQ ID NO 46
<211> LENGTH: 5
<212> TYPE: PRT
<213> ORGANISM: Artificial sequence
<220> FEATURE:
<223> OTHER INFORMATION: Synthetic sequence

<400> SEQUENCE: 46

Gly Ser Ser Ser Gly
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic sequence

<400> SEQUENCE: 47

Pro Lys Lys Lys Arg Lys Val
1               5

<210> SEQ ID NO 48
<211> LENGTH: 387
<212> TYPE: DNA
<213> ORGANISM: Artificial sequence
<220> FEATURE:
<223> OTHER INFORMATION: Synthetic sequence

<400> SEQUENCE: 48
atgaacaaat ctatcgagat caaagatcaa aacaacatag tcctgattga cagtcttgga    60
```

(-continued from previous; "Gly Gly Ser Gly Gly" at top of page under SEQ prior)

Gly Gly Ser Gly Gly
1               5

```
cagttcttta cagacatcga aaatgataat aacggtcgat ataacatcga ctacgtgctg    120
ctcaacgagg tagaacacga caatggcaac acgtactacg aagtgggcat gtatcggacc    180
gaagaggtac ccttttccga caaagtgacc caggacaatg tagaacttct ggaggataaa    240
tggctgcaaa tagatcaaca aggcgagagc tatgttgaaa gcattttttt tgagaacgaa    300
gaggacgcta gagaatatat taagttggtc ctgaagggtc atgagacatt tgaggaaacg    360
gctaaagcaa tcggagtcat caagtaa                                       387
```

<210> SEQ ID NO 49
<211> LENGTH: 129
<212> TYPE: PRT
<213> ORGANISM: Artificial sequence
<220> FEATURE:
<223> OTHER INFORMATION: Synthetic sequence

<400> SEQUENCE: 49

Met Asn Glu Leu Asn Asn Lys Met Ile Glu Asp Val Val Leu Gly Glu
1               5                   10                  15

Val Glu Leu Ile Glu Asp Leu Gly Gln Tyr Phe Ile Asp Ile Glu Gly
            20                  25                  30

Asp Tyr Glu Tyr Asn Val Glu Phe Ala Thr Leu Ser Glu Val Asp Tyr
        35                  40                  45

Lys Val Cys Ala Leu Tyr Glu Val Ala Thr Ser Lys Thr Tyr Glu Val
    50                  55                  60

Pro Tyr His Asp Lys Leu Glu Lys Glu Asp Met Lys Leu Phe Tyr Asp
65                  70                  75                  80

Lys Trp Leu Glu Lys Asp Gln Gln Glu Glu Thr Tyr Ile Glu Ser Val
                85                  90                  95

Phe Phe Val Asn Arg Glu Asp Ala Glu Ser Tyr Ile Lys Asp Val Leu
            100                 105                 110

Lys Gly Lys Glu Ser Leu Thr Glu Val Ala Ala Glu Ile Gly Tyr Phe
        115                 120                 125

Glu

<210> SEQ ID NO 50
<211> LENGTH: 390
<212> TYPE: PRT
<213> ORGANISM: Artificial sequence
<220> FEATURE:
<223> OTHER INFORMATION: Synthetic sequence

<400> SEQUENCE: 50

Ala Thr Gly Ala Ala Cys Gly Ala Ala Cys Thr Cys Ala Ala Thr Ala
1               5                   10                  15

Ala Thr Ala Ala Gly Ala Thr Gly Ala Thr Cys Gly Ala Ala Gly Ala
            20                  25                  30

Cys Gly Thr Thr Gly Thr Cys Cys Thr Cys Gly Gly Ala Gly Ala Gly
        35                  40                  45

Gly Thr Gly Gly Ala Gly Thr Thr Gly Ala Thr Ala Gly Ala Gly Gly
    50                  55                  60

Ala Thr Cys Thr Cys Gly Gly Thr Cys Ala Gly Thr Ala Thr Thr Thr
65                  70                  75                  80

Cys Ala Thr Ala Gly Ala Thr Ala Thr Ala Gly Ala Ala Gly Gly Ala
                85                  90                  95

Gly Ala Thr Thr Ala Cys Gly Ala Ala Thr Ala Thr Ala Ala Cys Gly
            100                 105                 110

-continued

```
Thr Ala Gly Ala Ala Thr Thr Thr Gly Cys Thr Ala Cys Gly Cys Thr
        115                 120                 125

Cys Ala Gly Cys Gly Ala Ala Gly Thr Ala Gly Ala Cys Thr Ala Thr
    130                 135                 140

Ala Ala Ala Gly Thr Cys Thr Gly Thr Gly Cys Thr Thr Thr Gly Thr
145                 150                 155                 160
Ala Thr Gly Ala Ala Gly Thr Ala Gly Cys Gly Ala Cys Gly Ala Gly
                165                 170                 175

Thr Ala Ala Gly Ala Cys Thr Thr Ala Cys Gly Ala Gly Gly Thr Gly
            180                 185                 190
Cys Cys Gly Thr Ala Cys Cys Ala Thr Gly Ala Thr Ala Ala Ala Thr
        195                 200                 205

Thr Gly Gly Ala Gly Ala Ala Gly Gly Ala Ala Gly Ala Thr Ala Thr
    210                 215                 220

Gly Ala Ala Gly Cys Thr Gly Thr Thr Cys Thr Ala Cys Gly Ala Thr
225                 230                 235                 240
Ala Ala Gly Thr Gly Gly Cys Thr Gly Gly Ala Gly Ala Ala Ala Gly
                245                 250                 255

Ala Cys Cys Ala Ala Cys Ala Gly Gly Ala Ala Gly Ala Ala Ala Cys
            260                 265                 270

Gly Thr Ala Cys Ala Thr Ala Gly Ala Ala Thr Cys Cys Gly Thr Gly
        275                 280                 285

Thr Thr Thr Thr Thr Cys Gly Thr Cys Ala Ala Thr Cys Gly Ala Gly
    290                 295                 300

Ala Ala Gly Ala Cys Gly Cys Thr Gly Ala Gly Ala Gly Thr Thr Ala
305                 310                 315                 320

Thr Ala Thr Ala Ala Ala Gly Gly Ala Thr Gly Thr Thr Thr Thr Gly
                325                 330                 335

Ala Ala Ala Gly Gly Ala Ala Ala Ala Gly Ala Gly Thr Cys Cys Cys
            340                 345                 350

Thr Gly Ala Cys Cys Gly Ala Gly Gly Thr Cys Gly Cys Gly Gly Cys
        355                 360                 365

Cys Gly Ala Gly Ala Thr Thr Gly Gly Thr Thr Ala Cys Thr Thr Thr
    370                 375                 380

Gly Ala Gly Thr Ala Ala
385                 390
```

MODULATORS OF CAS9 POLYPEPTIDES AND METHODS OF USE THEREOF

CROSS-REFERENCE

This application is a national stage filing under 35 U.S.C. § 371 of PCT/US2019/050214, filed Sep. 9, 2019, which application claims the benefit of U.S. Provisional Patent Application No. 62/729,295, filed Sep. 10, 2018, which applications are incorporated herein by reference in their entirety.

STATEMENT REGARDING FEDERALLY SPONSORED RESEARCH

This invention was made with government support under Grant No. HR0011-17-2-0043 awarded by the Defense Advanced Research Projects Agency, and Grant No. 1244557 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "BERK-396WO_SEQ_LISTING_ST25.txt" created on Sep. 4, 2019 and having a size of 61 KB. The contents of the text file are incorporated by reference herein in their entirety.

INTRODUCTION

Clustered Regularly Interspaced Short Palindromic Repeat (CRISPR)/Cas9 nucleases, when complexed with a guide RNA, effect genome editing in a sequence-specific manner RNA-guided Cas9 has proven to be a versatile tool for genome engineering in multiple cell types and organisms.

There is a need in the art for compositions and methods for controlling genome editing activity of CRISPR/Cas9.

SUMMARY

The present disclosure provides AcrIIA7 polypeptides, nucleic acids encoding the AcrIIA7 polypeptides, and kits comprising the AcrIIA7 polypeptides and/or nucleic acids encoding the AcrIIA7 polypeptides. The present disclosure provides methods of inhibiting enzymatic activity of a Cas9 polypeptide.

BRIEF DESCRIPTION OF THE DRAWINGS

FIG. 1 provides the amino acid sequence of an AcrIIA7 polypeptide.

FIG. 2 provides the nucleotide sequence encoding an AcrIIA7 polypeptide, where the nucleotide sequence is codon optimized for expression in human cells.

FIG. 3 provides an amino acid sequence of *Staphylococcus aureus* Cas9.

FIG. 4 provides an amino acid sequence of *Streptococcus pyogenes* Cas9.

FIG. 5 provides an amino acid sequence of *Streptococcus thermophilus* Cas9.

FIG. 6 provides an amino acid sequence of *Lactobacillus gasseri* Cas9.

DEFINITIONS

Figure 7:
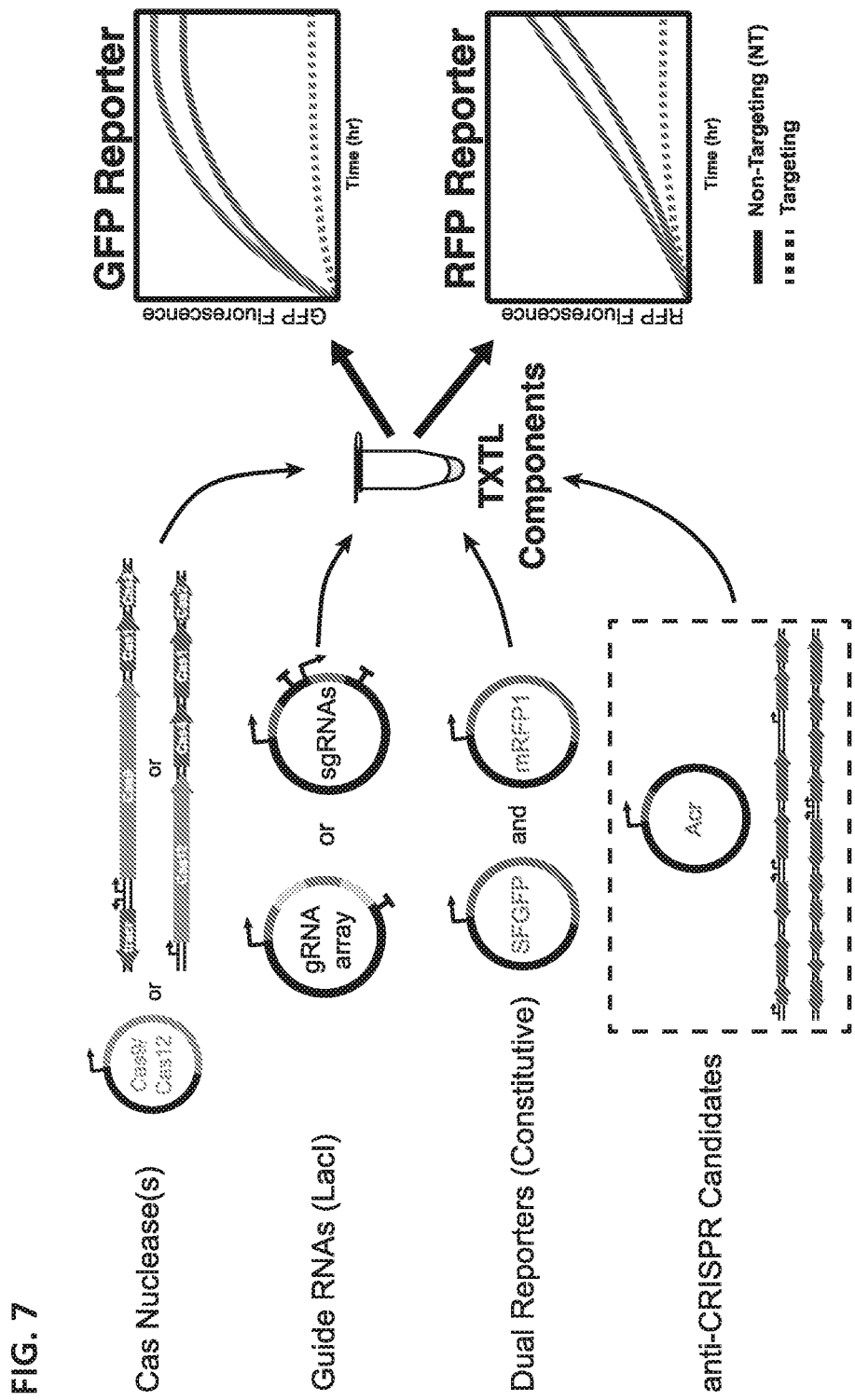
FIG. 7 is a schematic depiction of an assay used to identify proteins having anti-CRISPR/Cas9 activity.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 4 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi(dot)nlm(dot)nili(dot)gov/BLAST, ebi(dot)ac(dot)uk/Tools/msa/tcoffee/, ebi(dot)ac(dot)uk/Tools/msa/muscle/, mafft.cbrc(dot)jp/alignment/software/, www(dot)sbg(dot)bio(dot)ic(dot)ac(dot)uk/~phyre2/. See, e.g., Altschul et al. (1990), J. Mol. Bioi. 215:403-10.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., protein coding) and/or regulate translation of an encoded polypeptide.

As used herein, a "promoter" is a DNA regulatory region capable of binding RNA polymerase and initiating transcription of a downstream (3' direction) coding or non-coding sequence. Various promoters, including inducible promoters, may be used to drive the various nucleic acids (e.g., vectors) of the present disclosure.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ACRIIA7 polypeptide" includes a plurality of such polypeptides and reference to "the Cas9 polypeptide" includes reference to one or more Cas9 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides AcrIIA7 polypeptides, nucleic acids encoding the AcrIIA7 polypeptides, and kits comprising the AcrIIA7 polypeptides and/or nucleic acids encoding the AcrIIA7 polypeptides. The present disclosure provides methods of inhibiting an activity of a Cas9 polypeptide.

AcrIIA7 Polypeptides

The present disclosure provides AcrIIA7 polypeptides, where such polypeptides are inhibitors of Cas9 activity. An AcrIIA7 polypeptide of the present disclosure can inhibit binding and/or cleavage activity of a Cas9 polypeptide. An AcrIIA7 polypeptide of the present disclosure is also referred to herein as "an anti-CRISPR polypeptide," "an Acr polypeptide," "GF31 cand2" or "GF31-2."

An AcrIIA7 polypeptide of the present disclosure can comprise an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to a contiguous stretch of from about 50 amino acids to about 75 amino acids, from about 75 amino acids to about 100 amino acids, from about 100 amino acids to about 125 amino acids, from about 125 amino acids to about 150 amino acids, or from about 150 amino acids to about 187 amino acids, of the AcrIIA7 amino acid sequence depicted in FIG. 1 (SEQ ID NO:1).

In some cases, an AcrIIA7 polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the AcrIIA7 amino acid sequence depicted in FIG. 1 (SEQ ID NO:1).

An AcrIIA7 polypeptide of the present disclosure can have a length of from about 150 amino acids to about 187 amino acids. For example, an AcrIIA7 polypeptide of the present disclosure can have a length of from about 150 amino acids to about 155 amino acids, from about 155 amino acids to about 160 amino acids, from about 160 amino acids to about 165 amino acids, from about 165 amino acids to about 170 amino acids, from about 170 amino acids to about 175 amino acids, from about 175 amino acids to about 180 amino acids, or from about 180 amino acids to about 187 amino acids. In some cases, an AcrIIA7 polypeptide of the present disclosure can have a length of less than 150 amino acids. For example, in some cases, an AcrIIA7 polypeptide of the present disclosure has a length of from about 75 amino acids to about 150 amino acids. For example, in some cases, an AcrIIA7 polypeptide of the present disclosure has a length of from about 75 amino acids to about 100 amino acids, from about 100 amino acid to about 125 amino acids, or from about 125 amino acids to about 150 amino acids.

In some cases, an AcrIIA7 polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the AcrIIA7 amino acid sequence depicted in FIG. 1; and has a length of from about 150 amino acids to about 155 amino acids, from about 155 amino acids to about 160 amino acids, from about 160 amino acids to about 165 amino acids, from about 165 amino acids to about 170 amino acids, from about 170 amino acids to about 175 amino acids, from about 175 amino acids to about 180 amino acids, or from about 180 amino acids to about 187 amino acids.

In some cases, an Acr polypeptide of the present disclosure lacks the N-terminal 50 to 59 amino acids of the Acr amino acid sequence set forth in SEQ ID NO:1. In some cases, an Acr polypeptide of the present disclosure lacks the following amino acid sequence:

(SEQ ID NO: 11)
MRETIQRLLASNLSSNSIALATGVSQAVISKLRNAKKEIGNLSLNSAE

KLYNYQKGLEV.

In some cases, an Acr polypeptide of the present disclosure comprises an amino acid sequence having at least 50%, at least 55%, at least 60%, at least 65%, at least 70%, at least 75%, at least 80%, at least 85%, at least 90%, or at least 95%, to the amino acid sequence set forth in SEQ ID NO:1; lacks the N-terminal 50 to 59 amino acids of the Acr amino acid sequence set forth in SEQ ID NO:1; and has a length of about 128 amino acids (e.g., has a length of from 125 amino acids to 134 amino acids; e.g., has a length of 125 amino acids, 126 amino acids, 127 amino acids, 128 amino acids, 129 amino acids, 130 amino acids, 131 amino acids, 132 amino acids, 133 amino acids, or 134 amino acids).

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the following amino acid sequence:

(SEQ ID NO: 12)
MNKSIEIKDQNNIVLIDSLGQFFTDIENDNNGRYNIDYVLLNEVEHDN

GNTYYEVGMYRTEEVPFSDKVTQDNVELLEDKWLQIDQQGESYVESIF

FENEEDAREYIKLVLKGHETFEETAKAIGVIK;

and has a length of about 128 amino acids (e.g., e.g., has a length of from 125 amino acids to 134 amino acids; e.g., has a length of 125 amino acids, 126 amino acids, 127 amino acids, 128 amino acids, 129 amino acids, 130 amino acids, 131 amino acids, 132 amino acids, 133 amino acids, or 134 amino acids). An Acr having the amino acid sequence set forth in SEQ ID NO:12 is referred to in the Examples as "GF31-2-trunc."

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the following amino acid sequence:

(SEQ ID NO: 49)
MNELNNKMIEDVVLGEVELIEDLGQYFIDIEGDYEYNVEFATLSEVDY

KVCALYEVATSKTYEVPYHDKLEKEDMKLFYDKWLEKDQQEETYIESV

FFVNREDAESYIKDVLKGKESLTEVAAEIGYFE;

and has a length of about 129 amino acids (e.g., e.g., has a length of from 125 amino acids to 134 amino acids; e.g., has a length of 125 amino acids, 126 amino acids, 127 amino acids, 128 amino acids, 129 amino acids, 130 amino acids, 131 amino acids, 132 amino acids, 133 amino acids, or 134 amino acids). An Acr having the amino acid sequence set forth in SEQ ID NO:49 is referred to in the Examples as "GF31-2 hom."

In some cases, an AcrIIA7 polypeptide of the present disclosure inhibits binding and/or cleavage activity of a Cas9 polypeptide by at least 50%, at least 60%, at least 70%, at least 80%, at least 85%, at least 90%, at least 95%, at least 98%, or at least 99%, compared to the binding and/or cleavage activity of the Cas9 polypeptide in the absence of the AcrIIA7 polypeptide (i.e., where the Cas9 polypeptide is not contacted with the AcrIIA7 polypeptide).

In some cases, an AcrIIA7 polypeptide of the present disclosure inhibits binding and/or cleavage activity of a Cas9/guide RNA complex by at least 50%, at least 60%, at least 70%, at least 80%, at least 85%, at least 90%, at least 95%, at least 98%, or at least 99%, compared to the binding and/or cleavage activity of the Cas9/guide RNA complex in the absence of the AcrIIA7 polypeptide (i.e., where the Cas9/guide RNA complex is not contacted with the AcrIIA7 polypeptide).

In some cases, an AcrIIA7 polypeptide of the present disclosure inhibits cleavage activity of a Cas9/guide RNA complex by at least 50%, at least 60%, at least 70%, at least 80%, at least 85%, at least 90%, at least 95%, at least 98%, or at least 99%, compared to the cleavage activity of the Cas9/guide RNA complex in the absence of the AcrIIA7 polypeptide (i.e., where the Cas9/guide RNA complex is not contacted with the AcrIIA7 polypeptide).

In some cases, an Acr polypeptide of the present disclosure inhibits cleavage activity of a Cas9 polypeptide present in a Cas9/guide RNA complex by at least 50%, at least 60%, at least 70%, at least 80%, at least 85%, at least 90%, at least 95%, at least 98%, or at least 99%, compared to the cleavage activity of the Cas9 polypeptide in the absence of the Acr polypeptide, when the molar ratio of Acr to Cas9 polypeptide is at least 2:1, at least 5:1, or at least 10:1. In some cases, an Acr polypeptide of the present disclosure inhibits cleavage activity of a Cas9 polypeptide present in a Cas9/guide RNA complex by at least 50%, at least 60%, at least 70%, at least 80%, at least 85%, at least 90%, at least 95%, at least 98%, or at least 99%, compared to the cleavage activity of the Cas9 polypeptide in the absence of the Acr polypeptide, when the molar ratio of Acr to Cas9 polypeptide is from about 2:1 to about 5:1, from about 5:1 to about 10:1, from about 10:1 to about 20:1, or from about 20:1 to about 40:1.

"Binding" activity of a Cas9/guide RNA complex refers to binding of the Cas9/guide RNA complex to a target nucleic acid, where the target nucleic acid comprises a nucleotide sequence that has complementarity to a target-binding nucleotide sequence in the guide RNA.

"Cleavage" activity of a Cas9/guide RNA complex refers to generation by the Cas9/guide RNA complex of a single-strand or double-strand break in a target nucleic acid.

In some cases, an AcrIIA7 polypeptide of the present disclosure inhibits binding and/or cleavage activity of a Cas9 polypeptide having at least 50%, at least 60%, at least 70%, at least 80%, at least 85%, at least 90%, at least 95%, at least 98%, at least 99%, or 100%, amino acid sequence identity to the *Staphylococcus aureus* Cas9 amino acid sequence provided in FIG. 2.

In some cases, an AcrIIA7 polypeptide of the present disclosure does not substantially inhibit activity (e.g., cleavage activity) of a Cas9 having at least 50%, at least 60%, at least 70%, at least 80%, at least 85%, at least 90%, at least 95%, at least 98%, at least 99%, or 100%, amino acid sequence identity to the *Lactobacillus gasseri* amino acid sequence provided in FIG. 6.

In some cases, an AcrIIA7 polypeptide of the present disclosure does not substantially inhibit cleavage activity of *Streptococcus pyogenes* Cas9. For example, in some cases, an AcrIIA7 polypeptide of the present disclosure does not substantially inhibit cleavage activity of a Cas9/guide RNA complex, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 4. In some cases, an AcrIIA7 polypeptide of the present disclosure inhibits cleavage activity of a Cas9/guide RNA complex by no more than 20%, no more than 15%, no more than 10%, no more than 5%, no more than 2%, or no more than 1%, compared to the cleavage activity of the Cas9/guide RNA complex in the absence of the AcrIIA7 polypeptide, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 4. In some cases, an AcrIIA7 polypeptide of the present disclosure inhibits cleavage activity of a Cas9/guide RNA complex by less than 20%, less than 15%, less than 10%, less than 5%, less than 2%, or less than 1%, compared to the cleavage activity of the Cas9/guide RNA complex in the absence of the AcrIIA7 polypeptide, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 4.

Whether an AcrIIA7 polypeptide inhibits cleavage activity of a given Cas9 polypeptide present in a Cas9/guide RNA complex can be readily determined. For example, the effect of an AcrIIA7 polypeptide of the present disclosure on cleavage of a target DNA by a Cas9/guide RNA complex can be tested in a cell-free system in vitro, as described in the Examples section. For example, a target DNA is mixed in vitro with: a) a complex of Cas9 and a guide RNA, where the guide RNA comprises both a nucleotide sequence (tracrRNA) that activates the Cas9 polypeptide and a nucleotide sequence (crRNA) that binds to the target DNA; and b) an AcrIIA7 polypeptide. Production of cleavage products of action of the Cas9 on the target DNA can be detected by resolving the cleavage products on a 1% agarose cell and staining the resolved cleavage products.

As another example, the effect of an AcrIIA7 polypeptide of the present disclosure on cleavage of a target DNA by a Cas9/guide RNA complex can be tested in a cell. For example, a nucleic acid comprising a nucleotide sequence encoding an AcrIIA7 polypeptide and a nucleic acid comprising a nucleotide sequence encoding a reporter (e.g., a fluorescent protein such as a green fluorescent protein) can be integrated into the genome of a mammalian cell (e.g., 293 cells, or other mammalian cell line), generating a reporter cell; and a ribonucleoprotein (RNP) complex comprising a Cas9 polypeptide and a guide RNA targeting the nucleotide sequence encoding the reporter is introduced into the reporter cell. Inhibition of gene editing of the reporter can be determined by detecting the reporter. For example, where the reporter is a fluorescent protein, fluorescence activated cell sorting (FACS) can be used to determine whether gene editing has been inhibited. As another example, a mixture of a Cas9/guide RNA complex and AcrIIA7 polypeptide can be introduced into a mammalian cell line, and the effect of the AcrIIA7 polypeptide on the ability of the Cas9/guide RNA complex to carry out gene editing can be determined by analyzing production of a gene product encoded by a nucleotide sequence targeted by the guide RNA.

Covalently Linked Non-Peptidic Moiety

In some cases, an AcrIIA7 polypeptide of the present disclosure comprises a non-peptidic moiety covalently linked to the AcrIIA7 polypeptide. The covalently linked non-peptidic moiety can confer a desirable attribute (e.g., increased protease resistance, increased membrane permeability, increased in vivo half-life, increased in vivo stability, increased bioavailability), without substantially altering the ability of the linked AcrIIA7 polypeptide to inhibit Cas9 activity.

In some cases, the non-peptidic moiety confers increased in vivo half-life on the linked AcrIIA7 polypeptide, compared to the in vivo half-life of the AcrIIA7 not comprising the non-peptidic moiety. For example, in some cases, the in vivo half-life of an AcrIIA7 polypeptide comprising a covalently linked non-peptidic moiety is at least 10%, at least 25%, at least 50%, at least 2-fold, at least 5-fold, or at least 10-fold, greater than the in vivo half-life of the AcrIIA7 polypeptide not comprising the non-peptidic moiety. For example, in some cases, the non-peptidic moiety confers an increase in half-life of the linked AcrIIA7 polypeptide in circulation in an animal. In some cases, the non-peptidic moiety confers increased in vivo stability on the linked AcrIIA7 polypeptide, compared to the in vivo stability of the AcrIIA7 polypeptide not comprising the non-peptidic moiety. For example, in some cases, the in vivo stability of an AcrIIA7 polypeptide comprising a covalently linked non-peptidic moiety is at least 10%, at least 25%, at least 50%, at least 2-fold, at least 5-fold, or at least 10-fold, greater than the in vivo stability of the AcrIIA7 polypeptide not comprising the non-peptidic moiety. In some cases, the non-peptidic moiety confers increased bioavailability on the linked AcrIIA7 polypeptide, compared to the bioavailability of the AcrIIA7 polypeptide not comprising the non-peptidic moiety. For example, in some cases, the bioavailability of an AcrIIA7 polypeptide comprising a covalently linked non-peptidic moiety is at least 10%, at least 25%, at least 50%, at least 2-fold, at least 5-fold, or at least 10-fold, greater than the bioavailability of the AcrIIA7 polypeptide not comprising the non-peptidic moiety.

Suitable non-peptidic moieties include, but are not limited to, lipids and non-peptidic polymers. Suitable non-peptidic moieties include, but are not limited to, poly(ethylene glycol), polysialic acid, hydroxyethyl starch (HES), a dendrimer, a nanoparticle, and a liposome.

In some cases, a non-peptidic moiety covalently linked to an AcrIIA7 polypeptide of the present disclosure is a polymer. Polymers may contain one more of the following polyesters: homopolymers including glycolic acid units, referred to herein as "PGA"; lactic acid units, such as poly-L-lactic acid, poly-D-lactic acid, poly-D,L-lactic acid, poly-L-lactide, poly-D-lactide, and poly-D,L-lactide, collectively referred to herein as "PLA"; caprolactone units, such as poly(caprolactone), collectively referred to herein as "PCL"; copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain cases, the PEG region can be covalently associated with polymer to yield "PEGylated polymers" by a cleavable linker.

An AcrIIA7 polypeptide of the present disclosure may include one or more covalently linked hydrophilic polymers. Hydrophilic polymers include cellulosic polymers such as starch and polysaccharides; hydrophilic polypeptides; poly (amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly (hydroxyalkylmethacrylamide); poly(hydroxyalkylmethacrylate); poly(saccharides); poly(hydroxy acids); poly(vinyl alcohol); polyoxazoline; and copolymers thereof.

An AcrIIA7 polypeptide of the present disclosure may include one or more covalently linked hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

An AcrIIA7 polypeptide of the present disclosure may include one or more covalently linked biodegradable polymers. Suitable biodegradable polymers can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose such as methyl cellulose and ethyl cellulose, hydroxyalkyl celluloses such as hydroxypropyl cellulose, hydroxy-propyl methyl cellulose, and hydroxybutyl methyl cellulose, cellulose ethers, cellulose esters, nitro celluloses, cellulose acetate, cellulose propionate, cellulose acetate butyrate, cellulose acetate phthalate, carboxylethyl cellulose, cellulose triacetate, cellulose sulphate sodium salt, polymers of acrylic and methacrylic esters such as poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxyalkanoates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In some embodiments the particle contains biodegradable polyesters or polyanhydrides such as poly(lactic acid), poly(glycolic acid), and poly(lactic-co-glycolic acid).

Fusion Polypeptides

In some cases, an AcrIIA7 polypeptide is a fusion AcrIIA7 polypeptide. The present disclosure provides a fusion polypeptide (an "AcrIIA7 fusion polypeptide") comprising: a) an AcrIIA7 polypeptide of the present disclosure; and b) a heterologous fusion partner. The heterologous fusion partner can provide one or more desirable attributes (where such attributes include, e.g., as increased protease resistance, increased membrane permeability, or increased half-life, increased nuclear localization, and the like) without substantially altering the ability of the linked AcrIIA7 polypeptide to inhibit Cas9 activity. A fusion polypeptide comprising: a) an AcrIIA7 polypeptide of the present disclosure; and b) a heterologous fusion partner is also referred to herein as an "AcrIIA7 fusion polypeptide." A fusion polypeptide of the present disclosure can comprise two or more heterologous fusion partners.

Suitable heterologous fusion partners include, but are not limited to, a nuclear localization signal; a chloroplast transit peptide; an endosomal escape peptide; an epitope tag; a polypeptide that provides for ease of purification; a detectable protein; a protein that provides for increased in vivo half-life; and the like.

Suitable heterologous fusion partners include a hydroxine-binding protein, transthyretin, al-acid glycoprotein (AAG), transferrin, fibrinogen, albumin, an immunoglobulin, α-2-macroglobulin, a lipoprotein, and a fragment of any of the foregoing. Suitable heterologous fusion partners include a fluorescent protein, e.g., a green fluorescent protein (GFP), a yellow fluorescent protein, a red fluorescent protein a cyan fluorescent protein, and the like. Suitable heterologous fusion partners include, e.g., a poly(histidine) tag (e.g., a 6×His tag); a hemagglutinin (HA) tag; a FLAG tag; a Myc tag; and the like.

In some cases, a fusion polypeptide of the present disclosure comprises an AcrIIA7 polypeptide fused to a nuclear localization signal (NLS) (e.g., in some cases 2 or more, 3 or more, 4 or more, or 5 or more NLSs). Thus, in some cases, a fusion AcrIIA7 polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus of the AcrIIA7 polypeptide. In some cases, one or more NLSs (2 or more, 3 or more, 4 or more, or 5 or more NLSs) are positioned at or near (e.g., within 50 amino acids of) the N-terminus of the AcrIIA7 polypeptide. In some cases, one or more NLSs (2 or more, 3 or more, 4 or more, or 5 or more NLSs) are positioned at or near (e.g., within 50 amino acids of) the C-terminus of the AcrIIA7 polypeptide. In some cases, one or more NLSs (3 or more, 4 or more, or 5 or more NLSs) are positioned at or near (e.g., within 50 amino acids of) both the N-terminus and the C-terminus of the AcrIIA7 polypeptide. In some cases, an NLS is positioned at the N-terminus and an NLS is positioned at the C-terminus of the AcrIIA7 polypeptide.

Non-limiting examples of NLSs include an NLS sequence derived from: the NLS of the SV40 virus large T-antigen, having the amino acid sequence PKKKRKV (SEQ ID NO:47); the NLS from nucleoplasmin (e.g., the nucleoplasmin bipartite NLS with the sequence KRPAATKKAGQAKKKK (SEQ ID NO:13)); the c-myc NLS having the amino acid sequence PAAKRVKLD (SEQ ID NO:14) or RQRRNELKRSP (SEQ ID NO:15); the hRNPA1 M9 NLS having the sequence NQSSNFGPMKGGNFGGRSSGPYGGGGQYFAKPRNQGGY (SEQ ID NO:16); the sequence RMRIZFKNKGKDTAELRRRRVEVSVELRKAKKDEQILKRRNV (SEQ ID NO:17) of the IBB domain from importin-alpha; the sequences VSRKRPRP (SEQ ID NO:18) and PPKKARED (SEQ ID NO:19) of the myoma T protein; the sequence PQPKKKPL (SEQ ID NO:20) of human p53; the sequence SALIKKKKKMAP (SEQ ID NO:21) of mouse c-abl IV; the sequences DRLRR (SEQ ID NO:22) and PKQKKRK (SEQ ID NO:23) of the influenza virus NS1; the sequence RKLKKKIKKL (SEQ ID NO:24) of the Hepatitis virus delta antigen; the sequence REKKKFLKRR (SEQ ID NO:25) of the mouse Mx1 protein; the sequence KRKGDEVDGVDEVAKKKSKK (SEQ ID NO:26) of the human poly(ADP-ribose) polymerase; and the sequence RKCLQAGMNLEARKTKK (SEQ ID NO:27) of the steroid hormone receptors (human) glucocorticoid.

An AcrIIA7 fusion polypeptide of the present disclosure can include, as the fusion partner, a "Protein Transduction Domain" or PTD (also known as a CPP—cell penetrating peptide). Examples of PTDs include but are not limited to a minimal undecapeptide protein transduction domain (corresponding to residues 47-57 of HIV-1 TAT comprising YGRKKRRQRRR; SEQ ID NO:32); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:28); Transportan GWTLNSAGYLLGKINLKALAALAKKIL (SEQ ID NO:29); KALAWEAKLAKALAKA-LAKHLAKALAKALKCEA (SEQ ID NO:30); and RQIKIWFQNRRMKWKK (SEQ ID NO:31). Exemplary PTDs include but are not limited to, YGRKKRRQRRR (SEQ ID NO:32), RKKRRQRRR (SEQ ID NO:33); an arginine homopolymer of from 3 arginine residues to 50 arginine residues; Exemplary PTD domain amino acid sequences include, but are not limited to, any of the following: YGRKKRRQRRR (SEQ ID NO:32); RKKRRQRR (SEQ ID NO:34); YARAAARQARA (SEQ ID NO:35); THRLPRRRRRR (SEQ ID NO:36); and GGRRARRRRRR (SEQ ID NO:37). In some embodiments, the PTD is an activatable CPP (ACPP) (Aguilera et al. (2009) *Integr Biol* (Camb) June; 1(5-6): 371-381).

In some cases, an AcrIIA7 fusion polypeptide of the present disclosure comprises a linker between the AcrIIA7 polypeptide and the fusion partner. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. In some cases, the linker is proteolytically cleavable.

Examples of linker polypeptides include glycine polymers $(G)_n$, glycine-serine polymers (including, for example, $(GS)_n$, $GSGGS_n$ (SEQ ID NO:38), $GGSGGS_n$ (SEQ ID NO:39), and $GGGGS_n$ (SEQ ID NO:40), where n is an integer of at least one), glycine-alanine polymers, alanine-serine polymers. Exemplary linkers can comprise amino acid sequences including, but not limited to, GGSG (SEQ ID NO:41), GGSGG (SEQ ID NO:42), GSGSG (SEQ ID NO:43), GSGGG (SEQ ID NO:44), GGGSG (SEQ ID NO:45), GSSSG (SEQ ID NO:46), and the like.

An AcrIIA7 fusion polypeptide of the present disclosure can also comprise a covalently linked non-peptidic moiety, where suitable non-peptidic moieties are discussed above.

Nucleic Acids and Recombinant Expression Vectors

The present disclosure provides a nucleic acid comprising a nucleotide sequence encoding an AcrIIA7 polypeptide of the present disclosure. The present disclosure provides a recombinant expression vector comprising a nucleic acid comprising a nucleotide sequence encoding an AcrIIA7 polypeptide of the present disclosure. The present disclosure provides a nucleic acid comprising a nucleotide sequence encoding an AcrIIA7 fusion polypeptide of the present disclosure. The present disclosure provides a recombinant expression vector comprising a nucleic acid comprising a nucleotide sequence encoding an AcrIIA7 fusion polypeptide of the present disclosure.

The present disclosure provides a nucleic acid comprising a nucleotide sequence encoding an AcrIIA7 polypeptide of the present disclosure. In some cases, the nucleic acid is RNA. In some cases, the nucleic acid is DNA. The present disclosure provides a nucleic acid comprising a nucleotide sequence encoding an AcrIIA7 fusion polypeptide of the present disclosure. In some cases, the nucleic acid is RNA. In some cases, the nucleic acid is DNA.

In some cases, a nucleotide sequence encoding an AcrIIA7 polypeptide of the present disclosure is codon optimized. This type of optimization can entail a mutation of an AcrIIA7-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized AcrIIA7-encoding nucleotide sequence could be used. As another non-limiting example, if the intended host cell were a mouse cell, then a mouse codon-optimized AcrIIA7-encoding nucleotide sequence could be generated. As another non-limiting example, if the intended host cell were a plant cell, then a plant codon-optimized AcrIIA7-encoding nucleotide sequence could be generated. As another non-limiting example, if the intended host cell were an insect cell, then an insect codon-optimized AcrIIA7-encoding nucleotide sequence could be generated. A non-limiting example of a codon-optimized AcrIIA7-encoding nucleotide sequence is provided in FIG. 2.

As one example, a human codon-optimized nucleotide sequence encoding a truncated Acr (an Acr lacking the N-terminal 59 amino acids, as described above, is as follows:

```
                                       (SEQ ID NO: 48)
ATGAACAAATCTATCGAGATCAAAGATCAAAACAACATAGTCCTGATT

GACAGTCTTGGACAGTTCTTTACAGACATCGAAAATGATAATAACGGT

CGATATAACATCGACTACGTGCTGCTCAACGAGGTAGAACACGACAAT

GGCAACACGTACTACGAAGTGGGCATGTATCGGACCGAAGAGGTACCC

TTTTCCGACAAAGTGACCCAGGACAATGTAGAACTTCTGGAGGATAAA

TGGCTGCAAATAGATCAACAAGGCGAGAGCTATGTTGAAAGCATTTTT

TTTGAGAACGAAGAGGACGCTAGAGAATATATTAAGTTGGTCCTGAAG

GGTCATGAGACATTTGAGGAAACGGCTAAAGCAATCGGAGTCATCAAG

TAA.
```

As another example, a human codon optimized nucleotide sequence encoding the Acr referred to above as "GF31-2 hom" is as follows.

```
                                       (SEQ ID NO: 50)
ATGAACGAACTCAATAATAAGATGATCGAAGACGTTGTCCTCGGAGAG

GTGGAGTTGATAGAGGATCTCGGTCAGTATTTCATAGATATAGAAGGA

GATTACGAATATAACGTAGAATTTGCTACGCTCAGCGAAGTAGACTAT

AAAGTCTGTGCTTTGTATGAAGTAGCGACGAGTAAGACTTACGAGGTG

CCGTACCATGATAAATTGGAGAAGGAAGATATGAAGCTGTTCTACGAT

AAGTGGCTGGAGAAAGACCAACAGGAAGAAACGTACATAGAATCCGTG

TTTTTCGTCAATCGAGAAGACGCTGAGAGTTATATAAAGGATGTTTTG

AAAGGAAAAGAGTCCCTGACCGAGGTCGCGGCCGAGATTGGTTACTTT

GAGTAA.
```

In some cases, the nucleotide sequence encoding an AcrIIA7 polypeptide of the present disclosure, or encoding an AcrIIA7 fusion polypeptide of the present disclosure, is operably linked to one or more of a promoter, an enhancer, an internal ribosomal entry site, and a transcription termination signal.

In some cases, the nucleotide sequence encoding an AcrIIA7 polypeptide of the present disclosure, or encoding an AcrIIA7 fusion polypeptide of the present disclosure, is operably linked to a transcriptional control element. In some cases, the transcriptional control element is a transcriptional control element that is functional in a eukaryotic cell.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in a T cell, a B cell, a hematopoietic stem cell, a liver cell, a lung cell, a muscle cell (e.g., a cardiac muscle cell; a skeletal muscle cell), a retinal cell, or other targeted cell.

A suitable promoter can be a constitutively active promoter (i.e., a promoter that is constitutively in an active/"ON" state). A suitable promoter may be an inducible promoter (i.e., a promoter whose state, active/"ON" or inactive/"OFF", is controlled by an external stimulus, e.g., the presence of a particular temperature, compound, or protein). A suitable promoter can be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell).

In some cases, the promoter is a reversible promoter. Suitable reversible promoters, including reversible inducible promoters are known in the art. Such reversible promoters may be isolated and derived from any of a variety of organisms. Modification of reversible promoters derived from a first organism for use in a second (different) organism is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. A suitable promoter can include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. In some cases, the promoter is an insect-specific promoter. In some cases, the promoter is a plant-specific promoter. In some cases, the promoter is a protozoan-specific promoter.

In some cases, the promoter is a plant-specific promoter. Examples of plant promoters include, but are not limited to, a cauliflower mosaic virus (CaMV) promoter, a nopaline synthetase promoter, a ribose bisphosphate carboxylase promoter, a ubiquitin promoter, a UBQ3 promoter, a cestrum virus promoter, a rice actin 1 promoter, a CaMV 35S promoter, a CaMV 19S promoter, a sucrose synthase promoter, and a figwort mosaic virus promoter. Chemical agent-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-lapromoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257); copper-inducible system promoters; salicylate-inducible system promoters (e.g., the PR1a system); glucocorticoid-inducible promoters (Aoyama et al. (1997) *Plant J.* 11:605-612); and ecdysone-inducible system promoters. Tissue-preferred and tissue-specific promoters can be used to control expression in a particular plant tissue. Such tissue-preferred and tissue-specific promoters include leaf-preferred promoter, root-preferred promoters; root-specific promoters, seed-preferred promoters; seed-specific promoters; and the like.

As noted above, the present disclosure provides a recombinant expression vector comprising a nucleic acid comprising a nucleotide sequence encoding an AcrIIA7 polypeptide of the present disclosure. As noted above, the present disclosure provides a recombinant expression vector comprising a nucleic acid comprising a nucleotide sequence encoding an AcrIIA7 fusion polypeptide of the present disclosure.

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

Methods of introducing a nucleic acid (e.g., DNA or RNA) (e.g., a nucleic acid comprising a nucleotide sequence encoding an AcrIIA7 polypeptide of the present disclosure; a nucleic acid comprising a nucleotide sequence encoding an AcrIIA7 fusion polypeptide of the present disclosure; a nucleic acid encoding a Cas9 polypeptide; Cas9 guide RNA; a nucleic acid comprising a nucleotide sequence encoding a Cas9 guide RNA; a recombinant expression vector comprising one or more of the aforementioned nucleic acids; and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing a recombinant expression vector of the present disclosure into a cell or cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, an AcrIIA7 polypeptide-encoding nucleic acid can be provided as RNA. The RNA can be provided by direct chemical synthesis or may be transcribed in vitro from a DNA (e.g., encoding the AcrIIA7 polypeptide). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with a recombinant expression vector comprising a nucleic acid (e.g., a recombinant expression vector comprising a nucleic acid encoding an AcrIIA7 polypeptide; a recombinant expression vector comprising: i) a nucleic acid encoding an AcrIIA7 polypeptide; ii) a nucleotide sequence encoding a Cas9 polypeptide; and iii) a nucleotide sequence encoding a Cas9 guide RNA; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

A recombinant expression vector used for providing a nucleic acid comprising a nucleotide sequence encoding an AcrIIA7 polypeptide (and, optionally, encoding a Cas9 polypeptide and/or a Cas9 guide RNA) to a target host cell can include suitable promoters for driving the expression, that is, transcriptional activation, of the nucleic acid of interest. In other words, in some cases, the nucleic acid of interest will be operably linked to a promoter. In addition, recombinant expression vector used for providing a nucleic acid comprising a nucleotide sequence encoding an AcrIIA7 polypeptide (and, optionally, encoding a Cas9 polypeptide and/or a Cas9 guide RNA) to a cell may include nucleic acid sequences that encode for selectable markers in the target cells, so as to identify cells that have taken up the recombinant expression vector.

In some cases, an expression vector of the present disclosure comprises: a) a nucleotide sequence encoding an AcrIIA7 polypeptide of the present disclosure; and b) a nucleotide sequence encoding a Cas9 polypeptide (where the Cas9 polypeptide is one that can be inhibited by an AcrIIA7 polypeptide of the present disclosure, where such Cas9 polypeptides are described above). In some cases, the nucleotide sequence encoding the AcrIIA7 polypeptide and the nucleotide sequence encoding the Cas9 polypeptide are operably linked to the same promoter. In some cases, the nucleotide sequence encoding the AcrIIA7 polypeptide is operably linked to a first promoter; and the nucleotide sequence encoding the Cas9 polypeptide is operably linked to a second promoter, where the second promoter is different from the first promoter.

In some cases, an expression vector of the present disclosure comprises: a) a nucleotide sequence encoding an AcrIIA7 polypeptide of the present disclosure; b) a nucleotide sequence encoding a Cas9 polypeptide (where the Cas9 polypeptide is one that can be inhibited by an AcrIIA7 polypeptide of the present disclosure, where such Cas9 polypeptides are described above); and c) a nucleotide sequence encoding a Cas9 guide RNA. In some cases, the nucleotide sequence encoding the AcrIIA7 polypeptide, the nucleotide sequence encoding the Cas9 polypeptide, and the nucleotide sequence encoding the Cas9 guide RNA are operably linked to the same promoter. In some cases, the nucleotide sequence encoding the AcrIIA7 polypeptide is operably linked to a first promoter; and the nucleotide sequence encoding the Cas9 polypeptide and the nucleotide sequence encoding the Cas9 guide RNA are operably linked to a second promoter, where the second promoter is different from the first promoter.

Modified Host Cells

The present disclosure provides a modified host cell comprising an AcrIIA7 polypeptide of the present disclosure and/or a nucleic acid (e.g., a recombinant expression vector) comprising a nucleotide sequence encoding an AcrIIA7 polypeptide of the present disclosure. In some cases, the modified host cell is one that does not normally comprise an AcrIIA7 polypeptide of the present disclosure; i.e., the AcrIIA7 polypeptide is heterologous to the host cell.

The present disclosure provides a modified cell (e.g., a genetically modified cell) comprising nucleic acid comprising a nucleotide sequence encoding an AcrIIA7 polypeptide of the present disclosure. The present disclosure provides a genetically modified cell that is genetically modified with an mRNA comprising a nucleotide sequence encoding an AcrIIA7 polypeptide of the present disclosure. The present disclosure provides a genetically modified cell that is genetically modified with a recombinant expression vector comprising a nucleotide sequence encoding an AcrIIA7 polypeptide of the present disclosure. The present disclosure provides a genetically modified cell that is genetically modified with a recombinant expression vector comprising: a) a nucleotide sequence encoding an AcrIIA7 polypeptide of the present disclosure; b) a nucleotide sequence encoding a Cas9 polypeptide (where the Cas9 polypeptide is inhibited by an AcrIIA7 polypeptide of the present disclosure); and c) a nucleotide sequence encoding a Cas9 guide RNA.

A cell that serves as a recipient for an AcrIIA7 polypeptide of the present disclosure and/or a nucleic acid comprising a nucleotide sequence encoding an AcrIIA7 polypeptide of the present disclosure can be any of a variety of cells, including, e.g., in vitro cells; in vivo cells; ex vivo cells; primary cells; cancer cells; animal cells; plant cells; algal cells; fungal cells; insect cells; arachnid cells; etc. A cell that serves as a recipient for an AcrIIA7 polypeptide of the present disclosure and/or a nucleic acid comprising a nucleotide sequence encoding an AcrIIA7 polypeptide of the present disclosure is referred to as a "host cell" or a "target cell." A host cell or a target cell can be a recipient of an AcrIIA7 system of the present disclosure. A host cell or a target cell can be a recipient of a single component of an AcrIIA7 system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep, a horse, a camel); a rodent (e.g., a rat, a mouse); a non-human primate; a human; a feline (e.g., a cat); a canine (e.g., a dog); etc.) and the like. In some cases, the cell is a cell that does not originate from a natural organism (e.g., the cell can be a synthetically made cell; also referred to as an artificial cell).

A cell can be an in vitro cell (e.g., a cell in culture, e.g., an established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. HSCs can be induced in vitro to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other instances, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Compositions

The present disclosure provides a composition comprising an AcrIIA7 polypeptide of the present disclosure. The present disclosure comprises a composition comprising a nucleic acid or a recombinant expression vector comprising a nucleotide sequence encoding an AcrIIA7 polypeptide of the present disclosure. The present disclosure provides a composition comprising an AcrIIA7 fusion polypeptide of the present disclosure.

For example, one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, can be delivered (non-contemporaneously or simultaneously) using particles or lipids (e.g., liposomes). For example, any one of, or any combination of, (a)-(g) as set out above can be delivered associated with, or encapsulated in, a nanoparticle. For example, any one of, or any combination of, (a)-(g) as set out above can be delivered associated with, or encapsulated in, a lipid composition, e.g., a lipid composition (such as a liposome) comprising a lipid or lipidoid and a hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the lipid composition further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a lipid composition can be formed using a multistep process in which an AcrIIA7 polypeptide, a Cas9 polypeptide, and a Cas9 guideRNA are mixed together, e.g., at a 1:1:1 molar ratio, e.g., at room temperature, e.g., for 30 minutes, e.g., in sterile, nuclease free 1×phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

In some cases, one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, are delivered using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure. In one aspect, the aminoalcohol lipidoid compounds are combined with an agent (one or more of (a)-(f), above), to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, to a target cell.

In some cases, lipid nanoparticles (LNPs) are used to deliver one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N, N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(omega-methoxy-poly(ethylene glycol)2000) carbamoyl]-1,2-dimyristyloxlpropyl-3-amine (PEG-C-DOMG) may be used. A nucleic acid (e.g., a Cas9 guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure, to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012

134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm.

In some cases, nanoparticles suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell have a diameter of from 25 nm to 200 nm.

In some cases, nanoparticles suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell have a diameter of 100 nm or less. In some cases, nanoparticles suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell have a diameter of from 35 nm to 60 nm.

Nanoparticles suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. A prototype nanoparticle of semi-solid nature is the liposome.

In some cases, an exosome is used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. Exosomes are endogenous nano-vesicles that transport RNAs and proteins, and which can deliver RNA to the brain and other target organs.

In some cases, a liposome is used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000)carbamoyl]-1,2- dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) may be delivered encapsulated in PLGA microspheres such as that further described in US published applications 20130252281 and 20130245107 and 20130244279.

Supercharged proteins can be used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell (e.g., a target cell in vivo, where the target cell is a target cell in circulation, a target cell in a tissue, a target cell in an organ, etc.). An implantable device suitable for use in delivering a polypeptide and/or a nucleic acid (e.g., one or more of: a) recombinant expression vector comprising a nucleotide sequence encoding an AcrIIA7 polypeptide of the present disclosure or an AcrIIA7 fusion polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); e) a Cas9 guide RNA; f) a DNA comprising a nucleotide sequence encoding a Cas9 guide RNA; and g) an AcrIIA7 polypeptide or an AcrIIA7 fusion polypeptide of the present disclosure) to a target cell (e.g., a target cell in vivo, where the target cell is a target cell in circulation, a target cell in a tissue, a target cell in an organ, etc.) can include a container (e.g., a reservoir, a matrix, etc.) that comprises the polypeptide or nucleic acid (or combinations).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield a nucleic acid component from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear-auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

Systems

The present disclosure provides a system for controlling activity of a Cas9 polypeptide. A system of the present disclosure can comprise two or more of: a) an AcrIIA7 polypeptide of the present disclosure, an AcrIIA7 fusion polypeptide of the present disclosure, or a modified AcrIIA7 polypeptide of the present disclosure; b) an RNA comprising a nucleotide sequence encoding an AcrIIA7 polypeptide of the present disclosure or an AcrIIA7 fusion polypeptide of the present disclosure; c) a DNA comprising a nucleotide sequence encoding an AcrIIA7 polypeptide of the present disclosure or an AcrIIA7 fusion polypeptide of the present disclosure; d) a recombinant expression vector comprising a nucleic acid comprising a nucleotide sequence encoding an AcrIIA7 polypeptide of the present disclosure or an AcrIIA7 fusion polypeptide of the present disclosure; e) a Cas9 polypeptide (where the Cas9 polypeptide is one that can be inhibited by an AcrIIA7 polypeptide of the present disclosure, where such Cas9 polypeptides are described above); f) an RNA comprising a nucleotide sequence encoding a Cas9 polypeptide (where the Cas9 polypeptide is one that can be inhibited by an AcrIIA7 polypeptide of the present disclosure, where such Cas9 polypeptides are described above); g) a DNA comprising a nucleotide sequence encoding a Cas9 polypeptide (where the Cas9 polypeptide is one that can be inhibited by an AcrIIA7 polypeptide of the present disclosure, where such Cas9 polypeptides are described above); h) a recombinant expression vector comprising a nucleotide sequence encoding a Cas9 polypeptide (where the Cas9 polypeptide is one that can be inhibited by an AcrIIA7 polypeptide of the present disclosure, where such Cas9 polypeptides are described above); i) a Cas9 guide RNA; j) a DNA comprising a nucleotide sequence encoding a Cas9 guide RNA; k) a recombinant expression vector comprising a nucleotide sequence encoding a Cas9 guide RNA; l) a recombinant expression vector comprising a nucleotide sequence encoding a constant region (tracRNA region) of a Cas9 guide RNA and an insertion site for inserting a nucleotide sequence encoding a crRNA portion of the Cas9 guide RNA; m) a recombinant expression vector comprising: i) a nucleotide sequence encoding an AcrIIA7 polypeptide of the present disclosure; and ii) a nucleotide sequence encoding a Cas9 polypeptide (where the Cas9 polypeptide is one that can be inhibited by an AcrIIA7 polypeptide of the present disclosure, where such Cas9 polypeptides are described above); n) a recombinant expression vector comprising: i) a nucleotide sequence encoding an AcrIIA7 polypeptide of the present disclosure; and ii) a nucleotide sequence encoding a Cas9 polypeptide (where the Cas9 polypeptide is one that can be inhibited by an AcrIIA7 polypeptide of the present disclosure, where such Cas9 polypeptides are described above); and iii) a nucleotide sequence encoding a Cas9 guide RNA.

In some cases, a system of the present disclosure comprises two or more of: a) recombinant expression vector comprising a nucleotide sequence encoding an AcrIIA7 polypeptide of the present disclosure (where the recombinant expression vector may optionally include one or both of: i) a nucleotide sequence encoding a Cas9 polypeptide (where the Cas9 polypeptide is one whose activity can be inhibited by the AcrIIA7 polypeptide); and ii) a nucleotide sequence encoding a Cas9 guide RNA); b) a Cas9 polypeptide (where the Cas9 polypeptide is one whose activity can be inhibited by the AcrIIA7 polypeptide); c) a recombinant expression vector comprising a nucleotide sequence encoding a Cas9 polypeptide (where the Cas9 polypeptide is one whose activity can be inhibited by the AcrIIA7 polypeptide); d) an RNA comprising a nucleotide sequence encoding a Cas9 polypeptide (where the Cas9 polypeptide is one whose activity can be inhibited by the AcrIIA7 polypeptide); d) a Cas9 guide RNA; e) a DNA comprising a nucleotide sequence encoding a Cas9 guide RNA; and f) an AcrIIA7 polypeptide.

In some cases, a system of the present disclosure comprises: a) an AcrIIA7 polypeptide of the present disclosure; and b) a Cas9 polypeptide, where the Cas9 polypeptide is one that can be inhibited by the AcrIIA7 polypeptide. In some cases, a system of the present disclosure comprises: a) an AcrIIA7 polypeptide of the present disclosure; b) a Cas9 polypeptide, where the Cas9 polypeptide is one that can be inhibited by the AcrIIA7 polypeptide; and c) a Cas9 guide RNA. In some cases, a system of the present disclosure comprises: a) a recombinant expression vector comprising a nucleotide sequence encoding an AcrIIA7 polypeptide of the present disclosure; and b) a Cas9 polypeptide, where the Cas9 polypeptide is one that can be inhibited by the AcrIIA7 polypeptide. In some cases, a system of the present disclosure comprises: a) a recombinant expression vector comprising a nucleotide sequence encoding an AcrIIA7 polypeptide of the present disclosure; b) a Cas9 polypeptide, where the Cas9 polypeptide is one that can be inhibited by the AcrIIA7 polypeptide; and c) a Cas9 guide RNA. In some cases, a system of the present disclosure comprises: a) a recombinant expression vector comprising a nucleotide sequence encoding an AcrIIA7 polypeptide of the present disclosure; b) a recombinant expression vector comprising a nucleotide sequence encoding a Cas9 polypeptide, where the Cas9 polypeptide is one that can be inhibited by the AcrIIA7 polypeptide; and c) a Cas9 guide RNA. In some cases, a system of the present disclosure comprises: a) a ribonucleoprotein comprising: i) a Cas9 polypeptide, where the Cas9 polypeptide is one that can be inhibited by the AcrIIA7 polypeptide; and ii) a Cas9 guide RNA; and b) an AcrIIA7 polypeptide of the present disclosure. In some cases, a system of the present disclosure comprises: a) a ribonucleoprotein comprising: i) a Cas9 polypeptide, where the Cas9 polypeptide is one that can be inhibited by the AcrIIA7 polypeptide; and ii) a Cas9 guide RNA; and b) a recombinant expression vector comprising a nucleotide sequence encoding an AcrIIA7 polypeptide of the present disclosure.

AcrIIA7 Polypeptides

AcrIIA7 polypeptides that are suitable for inclusion in a system of the present disclosure include: a) AcrIIA7 polypeptides as described above; b) AcrIIA7 fusion polypeptides as described above; and c) modified AcrIIA7 polypeptides as described above. A system of the present disclosure can comprise an AcrIIA7 polypeptide of the present disclosure, or a nucleic acid or recombinant expression vector comprising a nucleotide sequence encoding an AcrIIA7 polypeptide of the present disclosure. A system of the present disclosure can comprise an AcrIIA7 fusion polypeptide of the present disclosure, or a nucleic acid or recombinant expression vector comprising a nucleotide sequence encoding an AcrIIA7 fusion polypeptide of the present disclosure. A system of the present disclosure can comprise a modified AcrIIA7 polypeptide of the present disclosure.

Cas9 Polypeptides

As noted above, in some cases, a system of the present disclosure includes a Cas9 polypeptide, where the Cas9 polypeptide is one that can be inhibited by an AcrIIA7 polypeptide of the present disclosure, where such Cas9 polypeptides are described above. In some cases, a system of the present disclosure comprises: a) an AcrIIA7 polypeptide of the present disclosure; and b) a Cas9 polypeptide, where the Cas9 polypeptide is one that can be inhibited by the AcrIIA7 polypeptide. In some cases, a system of the present disclosure comprises: a) an AcrIIA7 polypeptide of the present disclosure; b) a Cas9 polypeptide, where the Cas9 polypeptide is one that can be inhibited by the AcrIIA7 polypeptide; and c) a Cas9 guide RNA.

In some cases, a Cas9 polypeptide included in a system of the present disclosure comprises an amino acid sequence having at least 50%, at least 60%, at least 70%, at least 80%, at least 85%, at least 90%, at least 95%, at least 98%, at least 99%, or 100%, amino acid sequence identity to the *Staphylococcus aureus* Cas9 amino acid sequence provided in FIG. 2.

A *Staphylococcus aureus* Cas9 (SaCas9) suitable for inclusion in a system of the present disclosure can comprise one of the following sets of amino acid substitutions: N419A/R654A, Y211A/R654A, Y211A/Y212A, Y211A/N230A, Y211A/R245A, Y212A/Y230A, Y212A/R245A, Y230A/R245A, W229A/R654A, Y211A/Y212A/Y230A, Y211A/Y212A/R245A, Y211A/Y212A/Y651A, Y211A/Y230A/R245A, Y211A/Y230A/Y651A, Y211A/R245A/Y651A, Y211A/R245A/R654A, Y211A/R245A/N419A, Y211A/N419A/R654A, Y212A/Y230A/R245A, Y212A/Y230A/Y651A, Y212A/R245A/Y651A, Y230A/R245A/Y651A, R245A/N419A/R654A, T392A/N419A/R654A, R245A/T392AN419A/R654A, Y211A/R245A/N419A/R654A, W229A/R245A/N419A/R654A, Y211A/R245A/T392A/N419A/R654A, and Y211A1W229A/R245A/N419A/R654A.

A *Staphylococcus aureus* Cas9 (SaCas9) suitable for inclusion in a system of the present disclosure comprises one of the following amino acid substitutions or sets of amino acid substitutions: E782K; K929R; N968K; R1015H; E782K/N968K/R1015H (KKH variant); E782K/K929R/R1015H (KRH variant); or E782K/K929R/N968K/R1015H (KRKH variant).

In some cases, a Cas9 polypeptide comprising an amino acid sequence having at least 50%, at least 60%, at least 70%, at least 80%, at least 85%, at least 90%, at least 95%, at least 98%, at least 99%, or 100%, amino acid sequence identity to the *Lactobacillus gasseri* amino acid sequence provided in FIG. 6 is specifically excluded from a system of the present disclosure.

Cas9 Guide RNA

A nucleic acid molecule that binds to a Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also refer to a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence is taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases, the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et at, Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a Cas9 guide RNA comprises has one or more modifications, e.g., a base modification, a backbone modification, etc. Suitable nucleic acid modifications include, but are not limited to: 2'O-methyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)).

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a Cas9 guide RNA comprises a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable modifications include a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethyl-aminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Methods

The present disclosure provides methods of inhibiting activity of a Cas9 polypeptide. The methods generally involve contacting the Cas9 polypeptide with: a) an AcrIIA7 polypeptide of the present disclosure; b) an AcrIIA7 fusion polypeptide of the present disclosure; or b) a modified AcrIIA7 polypeptide of the present disclosure. In some cases, the contacting occurs in a living cell in vitro. In some cases, the contacting occurs in a living cell in vivo. In some cases, the contacting occurs outside of a cell in vivo (e.g., the contacting occurs in an extracellular fluid in vivo). For simplicity, unless stated otherwise, an "AcrIIA7 polypeptide of the present disclosure" includes an unmodified AcrIIA7 polypeptide, a variant AcrIIA7 polypeptide (as described above), an AcrIIA7 fusion polypeptide of the present disclosure, and a modified AcrIIA7 polypeptide of the present disclosure.

A method of the present disclosure can inhibit binding and/or cleavage activity of a Cas9/guide RNA complex by at least 50%, at least 60%, at least 70%, at least 80%, at least 85%, at least 90%, at least 95%, at least 98%, or at least 99%, compared to the binding and/or cleavage activity of the Cas9/guide RNA complex in the absence of the AcrIIA7 polypeptide (i.e., where the Cas9/guide RNA complex is not contacted with the AcrIIA7 polypeptide).

In some cases, a method of the present disclosure comprises introducing into a cell (a "target cell") a nucleic acid (e.g., a recombinant expression vector; an mRNA; and the like) comprising a nucleotide sequence encoding an AcrIIA7 polypeptide of the present disclosure, where the cell comprises, at the time the AcrIIA7-encoding nucleic acid is introduced into the cell, a Cas9 polypeptide (where the Cas9 polypeptide is one that can be inhibited by the AcrIIA7 polypeptide) or a nucleic acid comprising a nucleotide sequence encoding the Cas9 polypeptide. In some cases, the AcrIIA7-encoding nucleotide sequence is integrated into the genome of the cell. In some cases, the AcrIIA7-encoding nucleotide sequence is extrachromosomal.

In some cases, a method of the present disclosure comprises introducing into a cell (a "target cell") a nucleic acid (e.g., a recombinant expression vector; an mRNA; and the like) comprising a nucleotide sequence encoding an AcrIIA7 polypeptide of the present disclosure, where the cell does not comprise, at the time the AcrIIA7-encoding nucleic acid is introduced into the cell, a Cas9 polypeptide (where the Cas9 polypeptide is one that can be inhibited by the AcrIIA7 polypeptide) or a nucleic acid comprising a nucleotide sequence encoding the Cas9 polypeptide. In some cases, the AcrIIA7-encoding nucleotide sequence is integrated into the genome of the cell. In some cases, the AcrIIA7-encoding nucleotide sequence is extrachromosomal.

In some cases, a method of the present disclosure comprises introducing into a cell (a "target cell") an AcrIIA7 polypeptide of the present disclosure, where the cell comprises, at the time the AcrIIA7 polypeptide is introduced into the cell, a Cas9 polypeptide (where the Cas9 polypeptide is one that can be inhibited by the AcrIIA7 polypeptide) or a nucleic acid comprising a nucleotide sequence encoding the Cas9 polypeptide.

In some cases, a method of the present disclosure comprises introducing into a cell (a "target cell") an AcrIIA7 polypeptide of the present disclosure, where the cell does not comprise, at the time the AcrIIA7 polypeptide is introduced into the cell, a Cas9 polypeptide (where the Cas9 polypeptide is one that can be inhibited by the AcrIIA7 polypeptide) or a nucleic acid comprising a nucleotide sequence encoding the Cas9 polypeptide.

Where a method of the present disclosure comprises introducing into a cell a nucleic acid (e.g., a DNA; a recombinant expression vector; an RNA) comprising a nucleotide sequence encoding an AcrIIA7 polypeptide of the present disclosure, in some cases, the AcrIIA7-encoding nucleotide sequence is operably linked to one or more transcriptional control elements. In some cases, the one or more transcriptional control elements comprises a promoter, e.g., a promoter that is functional in a eukaryotic cell. In some cases, the promoter is a constitutive promoter. In some cases, the promoter is a regulated promoter, e.g., an inducible promoter. In some case, the inducible promoter is a drug-inducible promoter, and the method comprises contacting the cell with a drug that induces the drug-inducible promoter.

In some cases, a method of the present disclosure provides for controlling gene drive.

For example, where the gene drive limits viability of a target organism (or target population of an organism), a method of the present disclosure can restore viability to the target organism (or target population of an organism). Examples of target organisms (or target populations of an organism) include ticks (e.g., ticks that carry human pathogens), where ticks include ticks of the families Ixodidae and Argasidae, e.g., *Ixodes ricinus, I. rubicundus, I. scapularis, I. holocyclus,* and *I. pacificus* mites; mosquitoes (e.g., mosquitoes that carry human pathogens such as malaria parasites, Yellow Fever Virus, Dengue virus, Zika virus, Chikungunya virus, and the like), where examples of such mosquitoes include mosquitoes of the genera *Culex, Culistea, Aedes,* or *Anopheles,* e.g., *Aedes aegypti, Aedes albopictus,* and *Anopheles gamiae*; protozoans such as *Plasmodium* species (e.g., *Plasmodium falciparum, Plasmodium vivax, Plasmodium ovale, Plasmodium malariae, Plasmodium berghei, Plasmodium gallinaceum,* and *Plasmodium knowlesi*), nematode species, *Trypanosoma* species, *Trichomonadidae* species, *Leishmania* species, and the like; insects that are harmful to plants; arthropods that are harmful to plants; and the like.

In some cases, a method of the present disclosure provides for reducing off-target Cas9/guide RNA-mediated gene editing. In some cases, a method of the present disclosure reduces off-target Cas9/guide RNA-mediated gene editing by at least 10%, at least 15%, at least 20%, at least 25%, at least 50%, at least 75%, at least 80%, at least 90%, or more than 95%, compared to the extent of off-target Cas9/guide RNA-mediated gene editing when the Cas9 is not contacted with an AcrIIA7 polypeptide of the present disclosure.

In some cases, a method of the present disclosure provides protection against deleterious effects of a "hostile" Cas9/guide RNA. For example, an individual can comprise immune cells genetically modified to include an AcrIIA7-encoding nucleic acid; if such an individual comes into contact with a hostile Cas9/guide RNA complex that targets immune cells in a deleterious manner, such an individual can be protected from deleterious effects of such a hostile Cas9/guide RNA.

In some cases, an AcrIIA7 polypeptide of the present disclosure is used to deliver a Cas9 polypeptide to a cell, e.g., a eukaryotic cell. For example, in some cases, a complex of an AcrIIA7 polypeptide and a Cas9 polypeptide is delivered to a cell. The complex may further include a Cas9 guide RNA and/or a donor template.

Target Nucleic Acids and Cells

An AcrIIA7 polypeptide of the present disclosure inhibits a Cas9 polypeptide (when the Cas9 polypeptide is complexed with a Cas9 guide RNA) from binding and/or cleaving a target nucleic acid. target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the Cas9 guide RNA comprises a nucleotide sequence that hybridizes to a target sequence in a target nucleic acid, such that the target nucleic acid can be targeted).

A target nucleic acid (a target of a Cas9/guide RNA complex) can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh,* and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, adult cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising an AcrIIA7 polypeptide of the present disclosure or a nucleic acid (e.g., a recombinant expression vector) comprising a nucleotide sequence encoding an AcrIIA7 polypeptide of the present disclosure. The present disclosure provides a kit comprising an AcrIIA7 system of the present disclosure or a component of an AcrIIA7 system of the present disclosure.

A kit of the present can comprise: a) any combination of an AcrIIA7 system, as described above; b) and one or more additional components and/or reagents, e.g., i) a buffer; ii) a protease inhibitor; iii) a nuclease inhibitor; iv) a positive and/or negative control target DNA; v) a positive and/or negative control Cas9 guide RNA; and the like.

In some cases, a kit of the present disclosure comprises: a) a Cas9 polypeptide comprising an amino acid sequence having at least 70% amino acid sequence identity to the amino acid sequence depicted in FIG. 3, or a nucleic acid comprising a nucleotide sequence encoding the Cas9 polypeptide; and b) an AcrIIA7 polypeptide that is an inhibitor of an activity of the Cas9 polypeptide, wherein the AcrIIA7 polypeptide comprises an amino acid sequence having at least 70% (at least 70%, at least 85%, at least 80%, at least 85%, at least 90%, at least 95%, at least 98%, or 100%) amino acid sequence identity to the amino acid sequence depicted in FIG. 1, or a nucleic acid comprising a nucleotide sequence encoding the AcrIIA7 polypeptide, wherein the enzymatic activity is nucleic acid cleavage.

In some cases, a kit of the present disclosure comprises:
a) a Cas9 polypeptide comprising an amino acid sequence having at least 70% amino acid sequence identity to the amino acid sequence depicted in FIG. 3, or a nucleic acid comprising a nucleotide sequence encoding the Cas9 polypeptide; and b) i) an AcrIIA7 polypeptide that is an inhibitor of an activity of the Cas9 polypeptide; or ii) an AcrIIA7 fusion polypeptide of the present disclosure; or iii) a modified AcrIIA7 polypeptide of the present disclosure, wherein the AcrIIA7 polypeptide (or the AcrIIA7 polypeptide present in the fusion polypeptide, or the modified AcrIIA7 polypeptide)) comprises an amino acid sequence having at least 70% amino acid sequence identity to the amino acid sequence depicted in FIG. 1; or iv) a nucleic acid comprising a nucleotide sequence encoding the AcrIIA7 polypeptide; or v) a nucleic acid comprising a nucleotide sequence encoding the AcrIIA7 fusion polypeptide, wherein the enzymatic activity is nucleic acid cleavage.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-57 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A fusion polypeptide comprising:
a) anti-CRISPR (Acr) polypeptide that is an inhibitor of an enzymatic activity of a Cas9 polypeptide, wherein the Acr polypeptide comprises an amino acid sequence having at least 70% amino acid sequence identity to the amino acid sequence depicted in FIG. 1; and b) a heterologous fusion partner.

Aspect 2. The fusion polypeptide of aspect 1, wherein the heterologous fusion partner is a nuclear localization sequence.

Aspect 3. The fusion polypeptide of aspect 1, wherein the heterologous fusion partner is an epitope tag.

Aspect 4. The fusion polypeptide of any one of aspects 1-3, wherein the Acr polypeptide lacks the 50-59 amino-terminal amino acids of the polypeptide depicted in FIG. 1; and wherein the Acr polypeptide has a length of from 125 amino acids to 134 amino acids.

Aspect 5. A nucleic acid comprising a nucleotide sequence encoding the fusion polypeptide of any one of aspects 1-4.

Aspect 6. The nucleic acid of aspect 5, wherein the nucleotide sequence is operably linked to a promoter.

Aspect 7. A recombinant expression vector comprising the nucleic acid of aspect 5 or aspect 6.

Aspect 8. A cell comprising the nucleic acid of aspect 4 or aspect 5, or the recombinant expression vector of aspect 7.

Aspect 9. The cell of aspect 8, wherein the cell is a eukaryotic cell.

Aspect 10. The cell of aspect 8 or aspect 9, wherein the cell is in vitro.

Aspect 11. The cell of aspect 8 or aspect 9, wherein the cell is in vivo.

Aspect 12. A modified AcrIIA7 polypeptide comprising: a) an AcrIIA7 polypeptide that is an inhibitor of an enzymatic activity of a Cas9 polypeptide, wherein the AcrIIA7 polypeptide comprises an amino acid sequence having at least 70% amino acid sequence identity to the amino acid sequence depicted in FIG. 1; and b) a non-peptidic moiety covalently linked to the AcrIIA7 polypeptide.

Aspect 13. The modified AcrIIA7 polypeptide of aspect 12, wherein the non-peptidic moiety provides for one or more of an increase in in vivo half-life, in vivo stability, and bioavailability of the AcrIIA7 polypeptide, compared to the unmodified AcrIIA7 polypeptide.

Aspect 14. The modified AcrIIA7 polypeptide of aspect 12 or aspect 13, wherein the non-peptidic moiety comprises poly(ethylene glycol).

Aspect 15. A recombinant expression vector comprising a nucleotide sequence encoding an AcrIIA7 polypeptide that is an inhibitor of an enzymatic activity of a Cas9 polypeptide, wherein the AcrIIA7 polypeptide comprises an amino acid sequence having at least 70% amino acid sequence identity to the amino acid sequence depicted in FIG. 1.

Aspect 16. The recombinant expression vector of aspect 15, wherein the AcrIIA7 polypeptide-encoding nucleotide sequence is operably linked to a promoter.

Aspect 17. The recombinant expression vector of aspect 16, wherein the promoter is functional in a eukaryotic cell.

Aspect 18. The recombinant expression vector of aspect 16 or aspect 17, wherein the promoter is a regulated promoter.

Aspect 19. The recombinant expression vector of aspect 18, wherein the regulated promoter is an inducible promoter.

Aspect 20. The recombinant expression vector of aspect 19, wherein the inducible promoter is a heat-inducible promoter, a drug-inducible promoter, an alcohol-inducible promoter, a hormone-inducible promoter, a steroid-inducible promoter, or a metal-inducible promoter.

Aspect 21. The recombinant expression vector of aspect 16 or aspect 17, wherein the promoter is a tissue-specific promoter or a cell type-specific promoter.

Aspect 22. The recombinant expression vector of any one of aspects 15-21, further comprising a nucleotide sequence encoding a guide RNA that binds to and activates a Cas9 polypeptide.

Aspect 23. The recombinant expression vector of any one of aspects 15-22, wherein the recombinant expression vector is a recombinant viral vector.

Aspect 24. A cell comprising the recombinant expression vector of any one of aspects 15-23.

Aspect 25. The cell of aspect 24, wherein the cell is in vitro.

Aspect 26. The cell of aspect 24, wherein the cell is in vivo.

Aspect 27. The cell of any one of aspects 24-26, wherein the cell is a eukaryotic cell.

Aspect 28. The cell of aspect 27, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 29. A nucleic acid comprising:

a) a first nucleotide sequence encoding the constant region of a guide RNA;

b) a second nucleotide sequence encoding a Cas9 polypeptide; and c) a third nucleotide sequence encoding an AcrIIA7 polypeptide that is an inhibitor of the Cas9 polypeptide, wherein the AcrIIA7 polypeptide comprises an amino acid sequence having at least 70% amino acid sequence identity to the amino acid sequence depicted in FIG. 1.

Aspect 30. The nucleic acid of aspect 29, comprising an insertion site for inserting a nucleotide sequence encoding a guide sequence of the guide RNA, wherein the insertion site is 5' of and immediately adjacent to first nucleotide sequence.

Aspect 31. The nucleic acid of aspect 29, comprising a nucleotide sequence encoding a guide sequence of the guide RNA, wherein the guide sequence-encoding nucleotide sequence is 5' of and immediately adjacent to first nucleotide sequence.

Aspect 32. The nucleic acid of any one of aspects 29-31, wherein the Cas9 polypeptide comprises an amino acid sequence having at least 70% amino acid sequence identity to the amino acid sequence depicted in FIG. 3.

Aspect 33. The nucleic acid of any one of aspects 29-32, wherein the third nucleotide sequence is operably linked to a promoter.

Aspect 34. The nucleic acid of aspect 33, wherein the promoter is functional in a eukaryotic cell.

Aspect 35. The nucleic acid of aspect 33 or aspect 34, wherein the promoter is an inducible promoter.

Aspect 36. The nucleic acid of aspect 35, wherein the inducible promoter is a heat-inducible promoter, a drug-inducible promoter, an alcohol-inducible promoter, a hormone-inducible promoter, a steroid-inducible promoter, or a metal-inducible promoter.

Aspect 37. The nucleic acid of aspect 33 or 34, wherein the promoter is a tissue-specific promoter or a cell type-specific promoter.

Aspect 38. A recombinant expression vector comprising the nucleic acid of any one of aspects 29-37.

Aspect 39. A cell comprising the nucleic acid of any one of aspects 29-37 or the recombinant expression vector of aspect 38.

Aspect 40. The cell of aspect 39, wherein the cell is in vitro.

Aspect 41. The cell of aspect 39, wherein the cell is in vivo.

Aspect 42. The cell of any one of aspects 39-41, wherein the cell is a eukaryotic cell.

Aspect 43. The cell of aspect 42, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 44. A nucleic acid comprising a nucleotide sequence encoding an AcrIIA7 polypeptide that is an inhibitor of an enzymatic activity of a Cas9 polypeptide, wherein the AcrIIA7 polypeptide comprises an amino acid sequence having at least 70% amino acid sequence identity to the amino acid sequence depicted in FIG. 1, and wherein the nucleotide sequence is optimized for expression in a mammalian cell.

Aspect 45. The nucleic acid of aspect 44, wherein the nucleotide sequence is operably linked to a promoter.

Aspect 46. A recombinant expression vector comprising the nucleic acid of aspect 44 or aspect 45.

Aspect 47. A kit comprising:

a) a Cas9 polypeptide comprising an amino acid sequence having at least 70% amino acid sequence identity to the amino acid sequence depicted in FIG. 3, or a nucleic acid comprising a nucleotide sequence encoding the Cas9 polypeptide; and b) an AcrIIA7 polypeptide that is an inhibitor of an activity of the Cas9 polypeptide, wherein the AcrIIA7 polypeptide comprises an amino acid sequence having at least 70% amino acid sequence identity to the amino acid sequence depicted in FIG. 1, or a nucleic acid comprising a nucleotide sequence encoding the AcrIIA7 polypeptide, wherein the enzymatic activity is nucleic acid cleavage.

Aspect 48. The kit of aspect 47, wherein component (a) and component (b) are in separate containers.

Aspect 49. A method for inhibiting an activity of a Cas9 polypeptide, the method comprising contacting the Cas9 polypeptide with:

a) an AcrIIA7 polypeptide; or b) the AcrIIA7 fusion polypeptide of any one of aspects 1-4.

Aspect 50. The method of aspect 49, wherein the Cas9 polypeptide comprises an amino acid sequence having at least 70% amino acid sequence identity to the amino acid sequence depicted in FIG. 3.

Aspect 51. The method of aspect 49 or 50, wherein said contacting occurs in a living cell in vitro.

Aspect 52. The method of aspect 49 or 50, wherein said contacting occurs in a living cell in vivo.

Aspect 53. The method of aspect 51 or aspect 52, comprising introducing into the cell a nucleic acid comprising a nucleotide sequence encoding the AcrIIA7 polypeptide.

Aspect 54. The method of aspect 52, wherein the nucleotide sequence encoding the AcrIIA7 polypeptide is operably linked to an inducible promoter.

Aspect 55. The method of any one of aspects 51-54, wherein the cell is a eukaryotic cell.

Aspect 56. The method of aspect 54, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 57. The method of aspect 54, wherein the inducible promoter is a drug-inducible promoter, and wherein the method comprises contacting the cell with a drug that induces the drug-inducible promoter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

To identify a Cas9 inhibitory protein, bioinformatics was used to identify bacterial strains with CRISPR arrays containing spacers that target the genome, predicted mobile genetic elements in those strains, and screened fragments of the mobile genetic elements for anti-CRISPR activity. To test for activity, a cell-free transcription-translation system, as depicted schematically in FIG. 7, was used. Essentially, a reporter pair (e.g., two fluorescent proteins, such as green fluorescent protein (GFP) and red fluorescent protein (RFP) that is transcribed and translated over time was used. A Cas9 protein and gRNAs targeting the reporters were used to cleave the reporters, thereby reducing the fluorescence levels produced by the reporters. When linear DNA or plasmid DNA encoding a test protein was included, cleavage of the reporter was reduced, and therefore the fluorescence remained high, if the test protein inhibited the Cas9.

Figure 8:
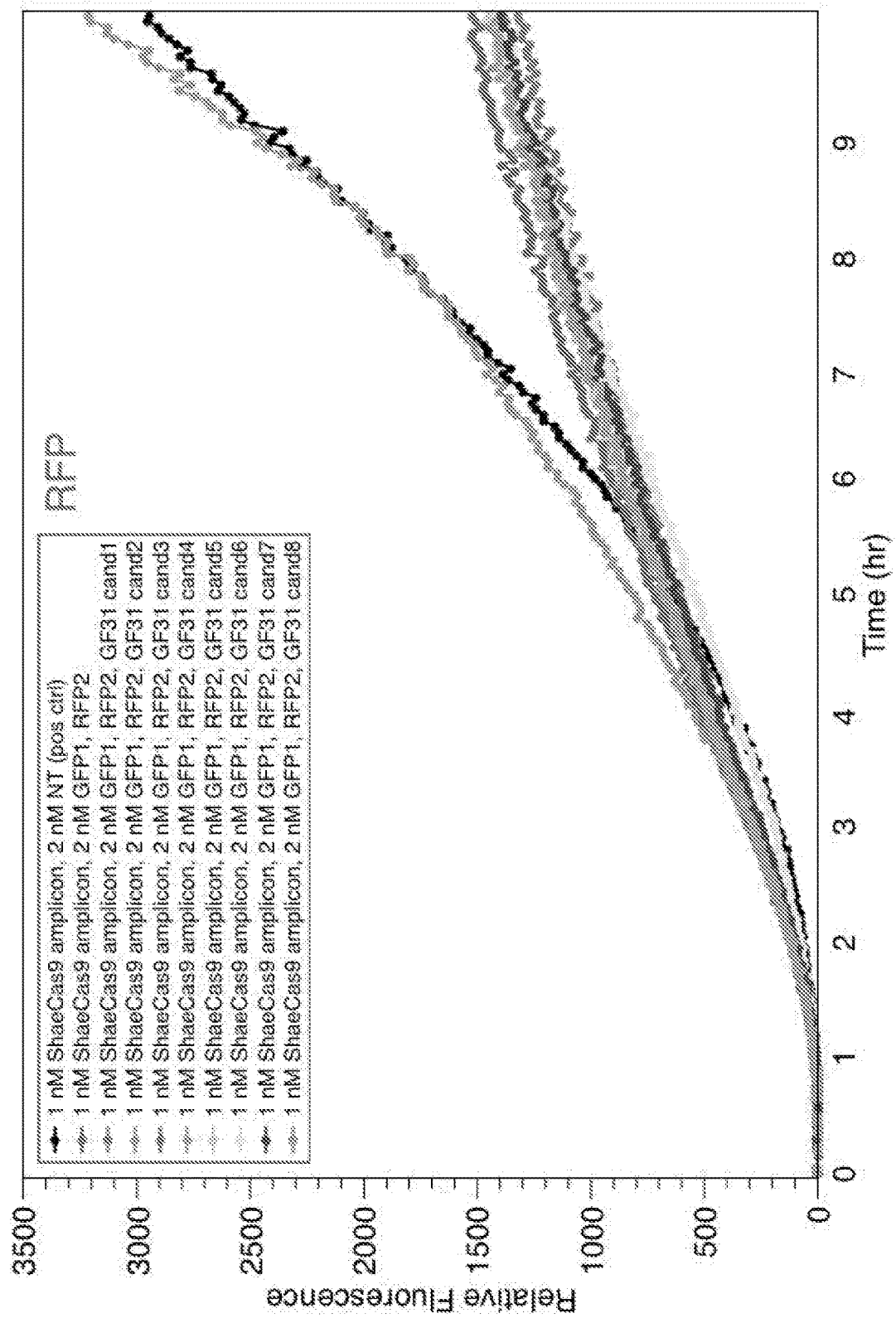
FIG. 8 depicts the effects of various candidate anti-CRISPR proteins (cand1 through cand8 on Cas9/guide RNA-mediated cleavage of a target nucleic acid encoding a fluorescent protein.

As shown in FIG. 8, RFP reporter and candidate proteins from genomic fragment 31 (GF31) were identified as potential Cas9 inhibitors during screening of mobile genetic element DNA fragments. The candidate protein designated "GF31 cand2" was identified as a protein that exhibited anti-CRISPR activity; this candidate protein was termed AcrIIA7.

Figure 9:
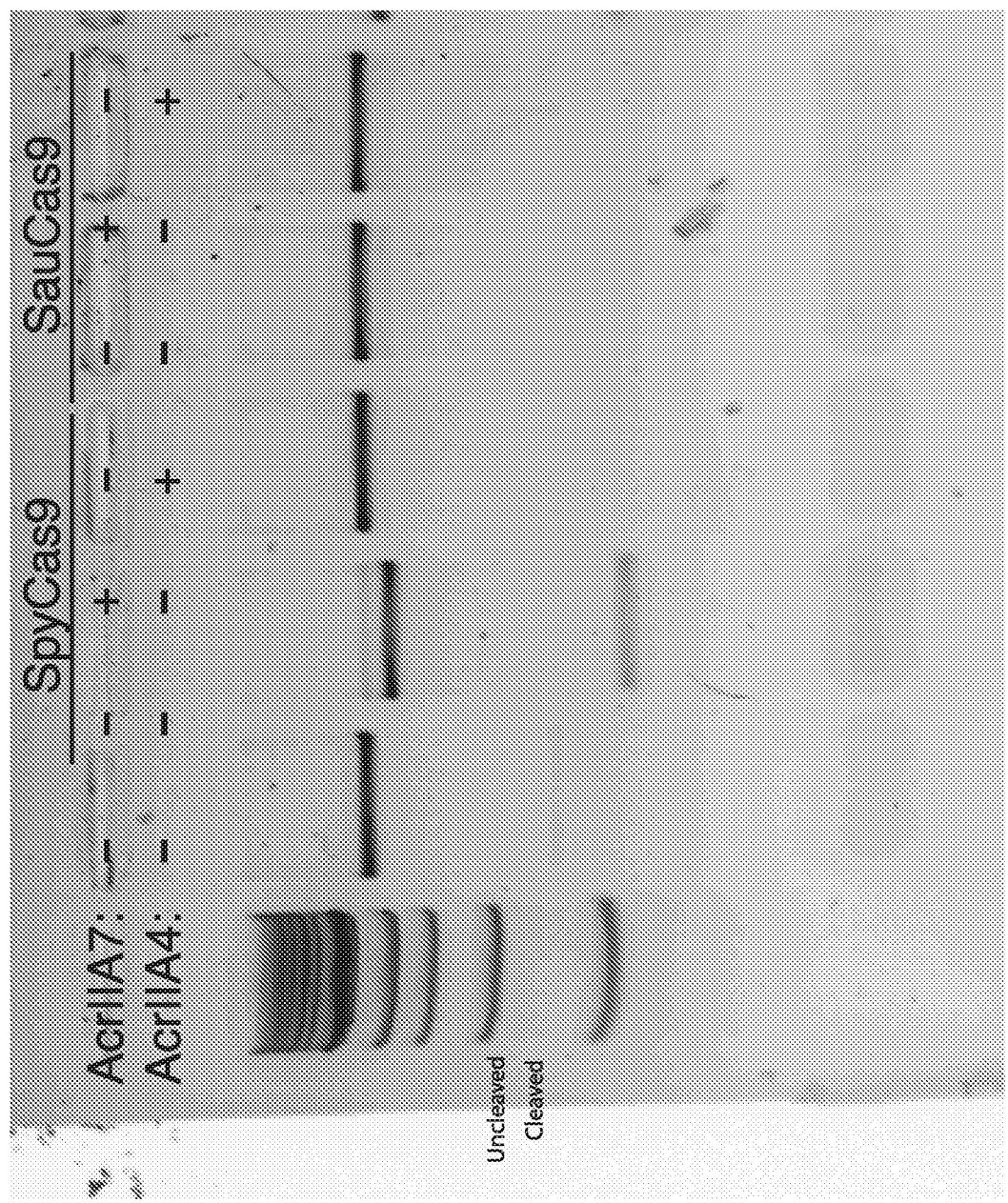
FIG. 9 depicts the effect of anti-CRISPR protein AcrIIA7 on SauCas9/guide and SpyCas9/guide RNA-mediated cleavage of a target nucleic acid a cell-free in vitro.

The AcrIIA7 protein was purified and tested for its ability to inhibit *Staphylococcus aureus* Cas9 (SauCas9) or *Streptococcus pyogenes* Cas9 (SpyCas9) cleavage in vitro. The results are shown in FIG. 9. AcrIIA4 is a well-characterized anti-CRISPR for SpyCas9, and which does not inhibit SauCas9, and was used as a positive control for inhibition of Spy Cas9. As shown in FIG. 9, AcrIIA7 inhibits SauCas9 activity, but does not substantially inhibit SpyCas9.

Figure 10:
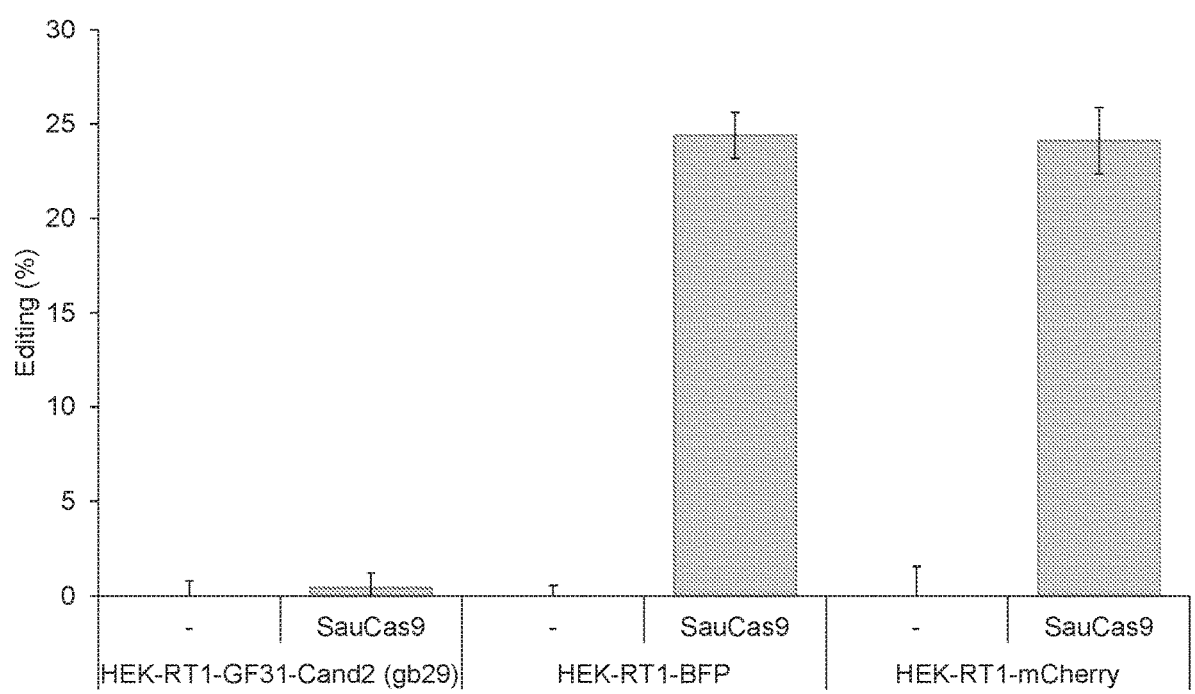
FIG. 10 depicts the effect of anti-CRISPR protein AcrIIA7 on Cas9/guide RNA-mediated cleavage of a target nucleic acid in a mammalian cell.

The ability of AcrIIA7 to inhibit SauCas9 in a mammalian cell was tested. A nucleic acid encoding AcrIIA7, as well as a nucleic acid encoding either blue fluorescent protein (BFP) or the fluorescent protein mCherry, were integrated into the genome of a mammalian cell line (HEK). SauCas9 targeting eGFP was delivered into the modified HEK cell lines. SauCas9 and guide RNA were provided to the cell as a preassembled ribonucleoprotein (RNP) complex. After a few days, fluorescence produced by the GFP or mCherry was measured. As shown in FIG. 10, GF31 cand2 (AcrIIA7) inhibited Cas9/guide RNA-mediated editing, while the controls did not.

Materials and Methods

The following guide RNAs (gRNA) can be used, together with Sth1 Cas9, Sau Cas9, Lga Cas9, or Spy Cas9, to target the Cas9 to enhanced GFP (eGFP).

```
Sth1Cas9 gRNA (targets eGFP in human cells)
                                        (SEQ ID NO: 7)
gccttcgggcatggcggacttGTTTTTGTACTCTCAAGATTCAATAAT

CTTGCAGAAGCTACAAAGATAAGGCTTCATGCCGAAATCAACACCCTG

TCATTTTATGGCAGGGTGTTTCG

SauCas9 gRNA (targets eGFP in human cells)
                                        (SEQ ID NO: 8)
gcaagggcgaggagctgttcacGTTTTAGTACTCTGGAAACAGAATCT

ACTAAAACAAGGCAAAATGCCGTGTTTATCTCGTCAACTTGTTGGCGA

GATTTTT

LgaCas9 gRNA (targets eGFP in human cells)
                                        (SEQ ID NO: 9)
ggtcgagctggacggcgacGTTTTAGATGGTTGTTAGgaaaCTAACAA

CCAGATTTAAAATCAAGCAATGCATCTTTTGATGCAAAGTTTCAATAC

TTGTCCCGAGCTATCGAGGGAC

SpyCas9 crRNA (targets eGFP in human cells, part
of Alt-R system in IDT, pairs with tracrRNA)
                                        (SEQ ID NO: 10)
ctgaagttcatctgcaccacGTTTTAGAGCTATCT
```

Example 2

Figure 11:
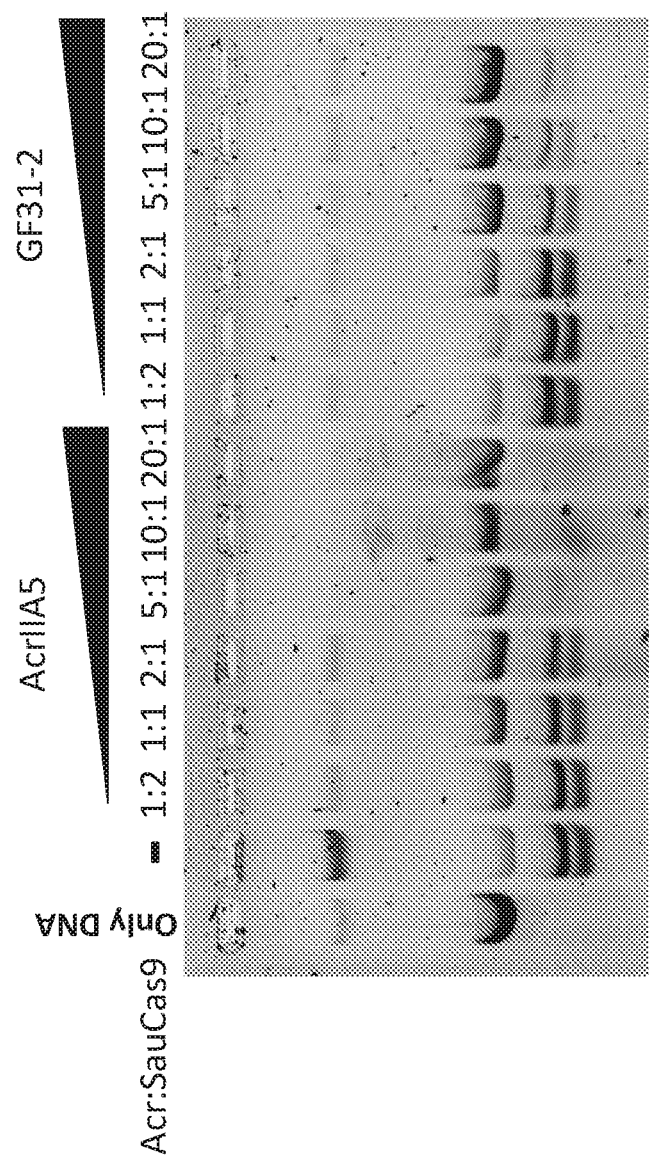
FIG. 11 depicts the effect of anti-CRISPR protein GF31-2 compared to the AcrIIA5 anti-CRISPR on SauCas9/guide RNA-mediated cleavage of a target nucleic acid at various molar ratios of GF31-2:SauCas9 and AcrIIA5:SauCas9 in vitro.

Inhibition of *S. aureus* Cas9 ("SauCas9") by Acrs AcrIIA5 and GF31-2 (AcrIIA7) at various ratios of Acr to SauCas9 was tested. The data are shown in FIG. 11. AcrIIA5 inhibits both *S. pyogenes* Cas9 and *S. aureus* Cas9. Hynes et al. (2017) *Nat. Microbiol.* 2:1374. As shown in FIG. 11, GF31-2 inhibited SauCas9-mediated cleavage of target DNA at GF31-2:SauCas9 molar ratios of 5:1, 10:1, and 20:1.

Figure 12:
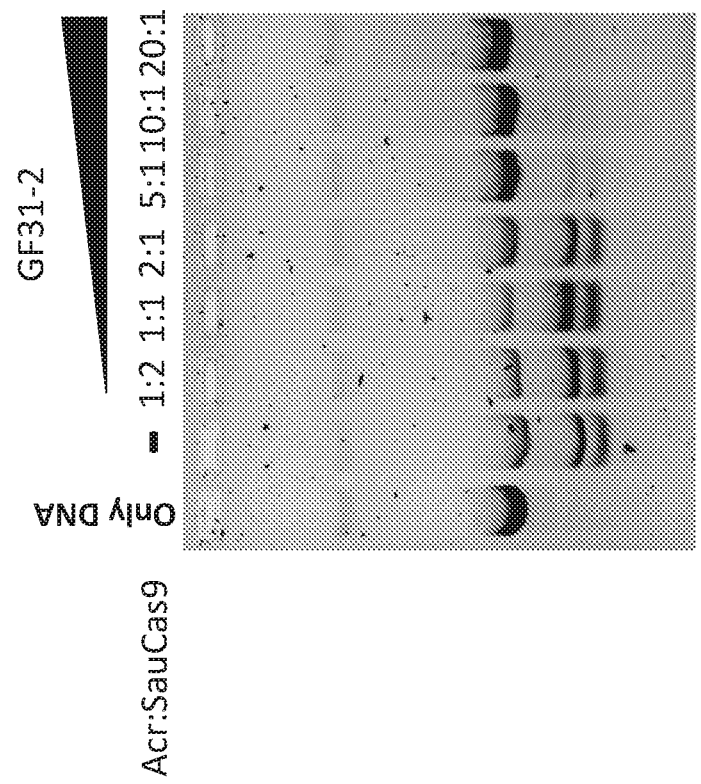
FIG. 12 depicts the effect of a truncated form of anti-CRISPR protein GF31-2 on SauCas9/guide RNA-mediated cleavage of a target nucleic acid at various molar ratios of truncated GF31-2:SauCas9 in vitro.

The effect of removal of the N-terminal 59 amino acids from AcrIIA7 (GF31-2) on inhibition of SauCas9 was tested. The results are shown in FIG. 12. Various ratios of truncated GF31-2:SauCas9 were tested. As shown in FIG. 12, truncated GF31-2 inhibited SauCas9-mediated cleavage of target DNA at truncated GF31-2:SauCas9 molar ratios of 5:1, 10:1, and 20:1.

Figure 13:
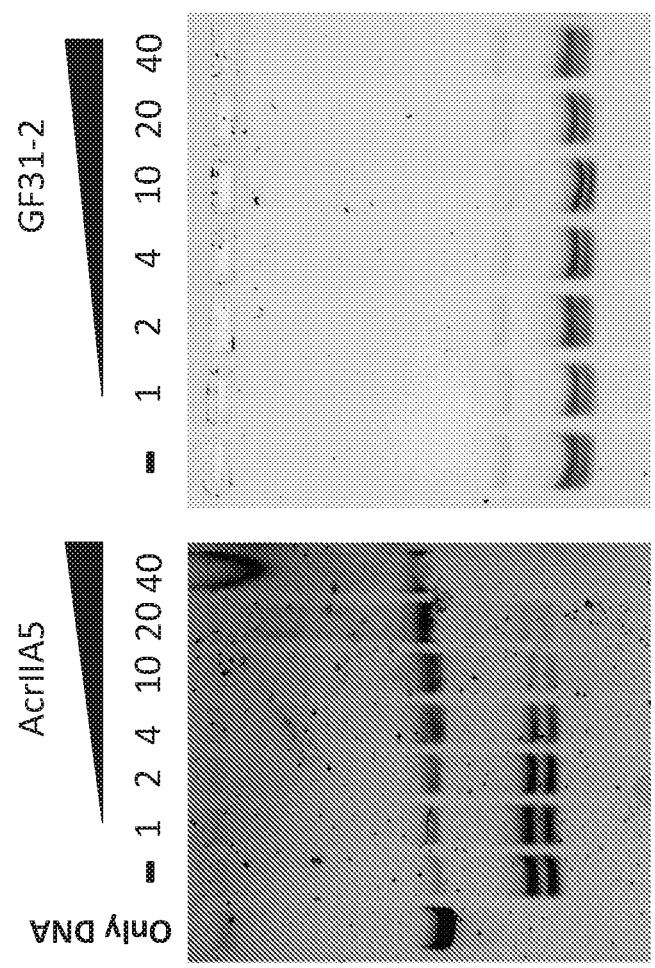
FIG. 13 depicts the effect of a truncated form of anti-CRISPR protein GF31-2 on SpyCas9/guide RNA-mediated cleavage of a target nucleic acid at various molar fold excess of GF31-2 over SpyCas9.

The truncated form of GF31-2 did not inhibit *S. pyogenes* Cas9 (SpyCas9). The data are shown in FIG. 13. The truncated form of GF31-2 was incubated with SpyCas9 at the indicated fold molar excess of truncated GF31-2 over SpyCas9 As shown in FIG. 13, truncated GF31-2 did not inhibit SauCas9-mediated cleavage of target DNA, even at 40-fold molar excess over SpyCas9.

Example 3

The effect of Acrs on Cas9-mediated cleavage of a target genomic nucleic acid in a mammalian cell was tested. The data are shown in FIG. 14-16.

Figure 14:
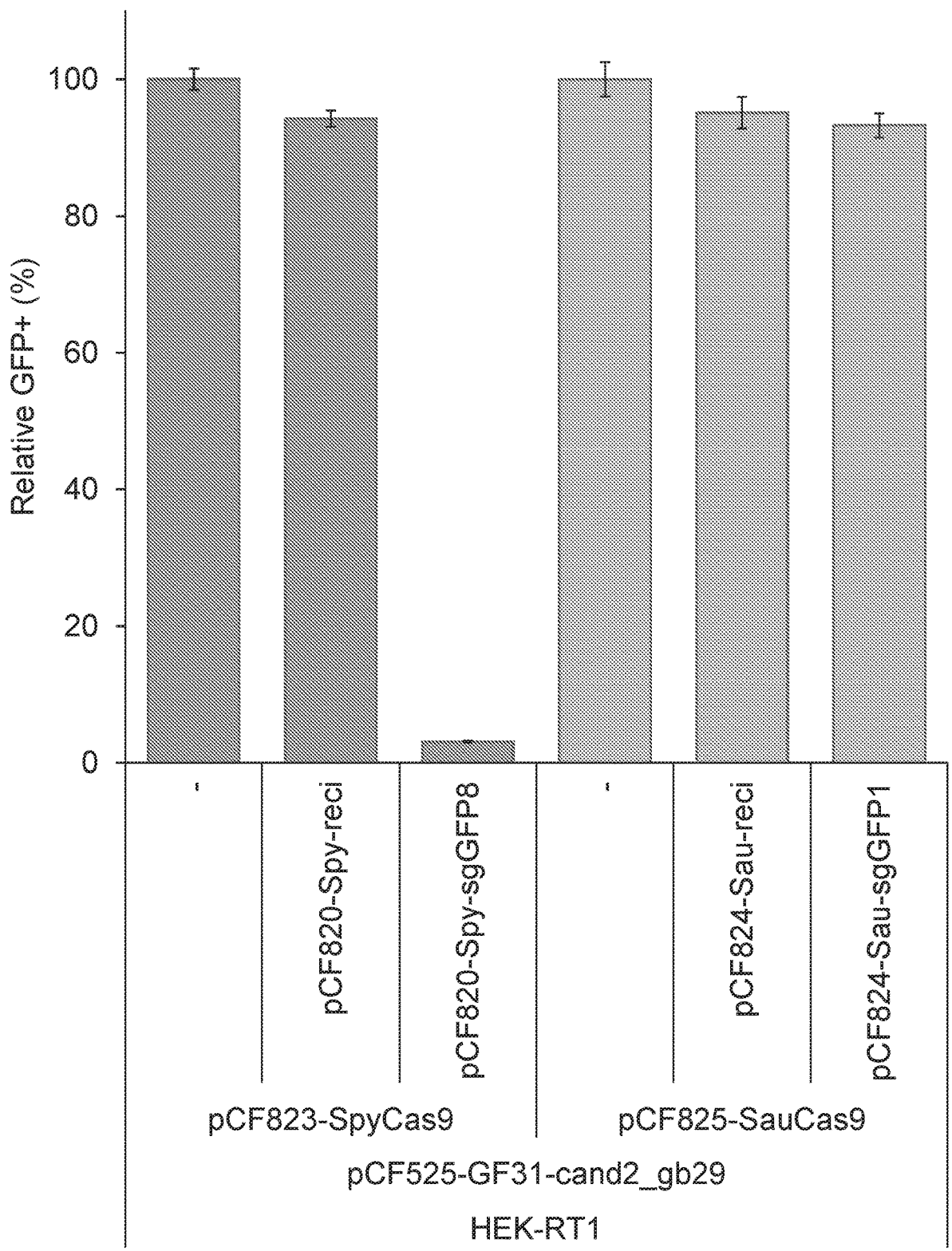
FIG. 14 depicts the effect of anti-CRISPR protein GF31-cand2 on *S. pyogenes* (SpyCas9)/guide RNA-mediated and *S. aureus* (SauCas9)/guide RNA-mediated cleavage of a genomic target nucleic acid in a mammalian cell.

FIG. 14 depicts the effect of anti-CRISPR protein GF31-cand2 (gb29; a.k.a. GF31-2 or AcrIIA7) on *S. pyogenes* (SpyCas9)/guide RNA-mediated and *S. aureus* (SauCas9)/guide RNA-mediated cleavage of a genomic target nucleic acid in a mammalian cell. The data show the efficiency of Acr-mediated inhibition of genomic GFP disruption by SpyCas9 or SauCas9 with a guide RNA targeting GFP, in a human cell line. The various Cas9 and guide RNAs were expressed from separate, stably integrated lentiviral vectors. The anti-CRISPR protein was expressed from a stably integrated lentiviral vector. The reporter GFP was expressed from a stably integrated lentiviral vector under control of a doxycycline-inducible promoter. GF31-cand2 strongly inhibited SauCas9 but not SpyCas9 in mammalian cells.

Figure 15:
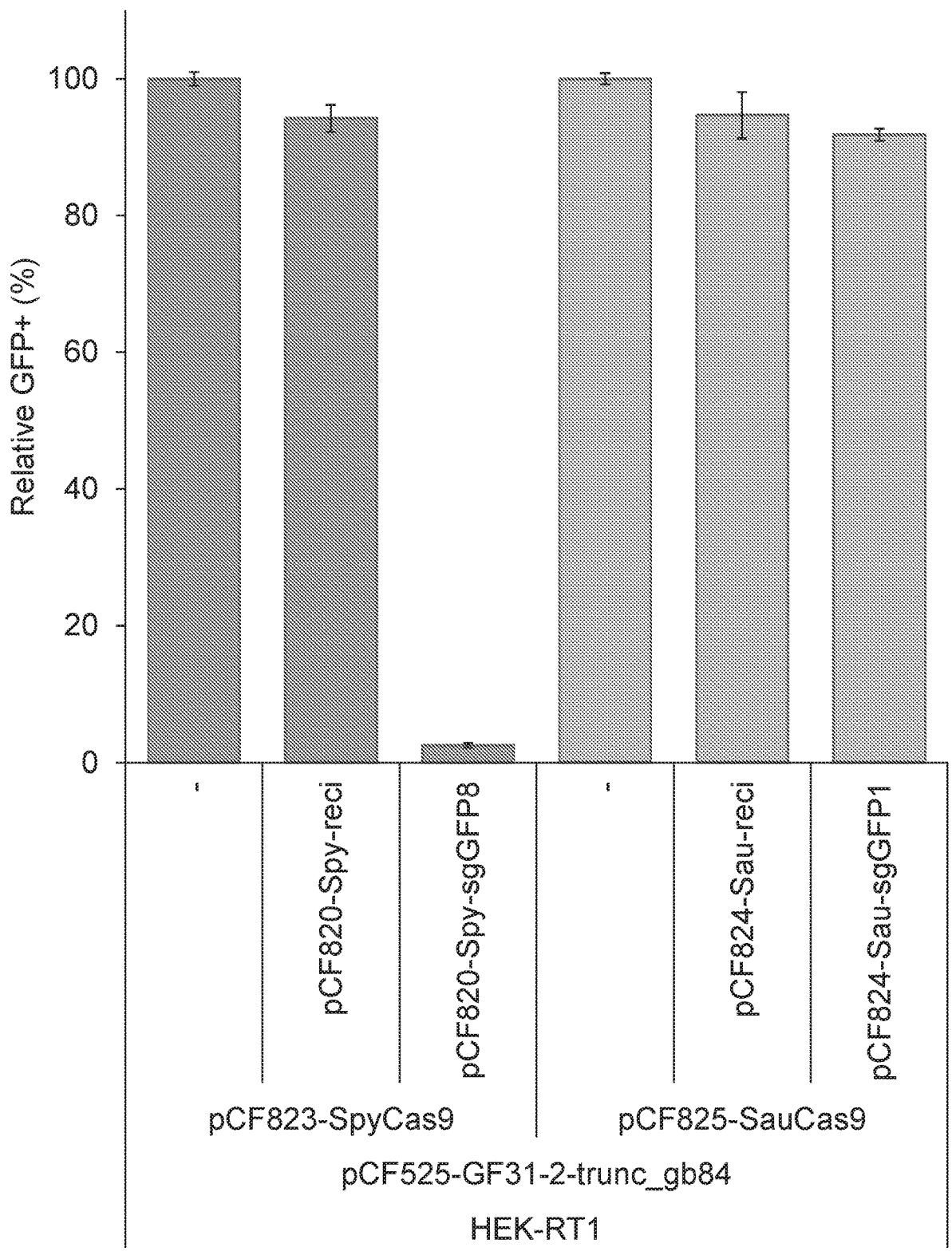
FIG. 15 depicts the effect of anti-CRISPR protein GF31-2-trunc (gb84; truncated version of GF31-cand2) on *S. pyogenes* (SpyCas9)/guide RNA-mediated and *S. aureus* (SauCas9)/guide RNA-mediated cleavage of a genomic target nucleic acid in a mammalian cell.

FIG. 15 depicts the effect of anti-CRISPR protein GF31-2-trunc (gb84; truncated version of GF31-cand2) on *S. pyogenes* (SpyCas9)/guide RNA-mediated and *S. aureus* (SauCas9)/guide RNA-mediated cleavage of a genomic target nucleic acid in a mammalian cell. The data show the efficiency of Acr-mediated inhibition of genomic GFP disruption by SpyCas9 or SauCas9 with a respective guide RNA targeting GFP, in a human cell line. The various Cas9 and guide RNAs were expressed from separate, stably integrated lentiviral vectors. The anti-CRISPR protein was expressed from a stably integrated lentiviral vector. The reporter GFP was expressed from a stably integrated lentiviral vector under control of a doxycycline-inducible promoter. GF31-2-trunc strongly inhibited SauCas9 but not SpyCas9 in mammalian cells.

Figure 16:
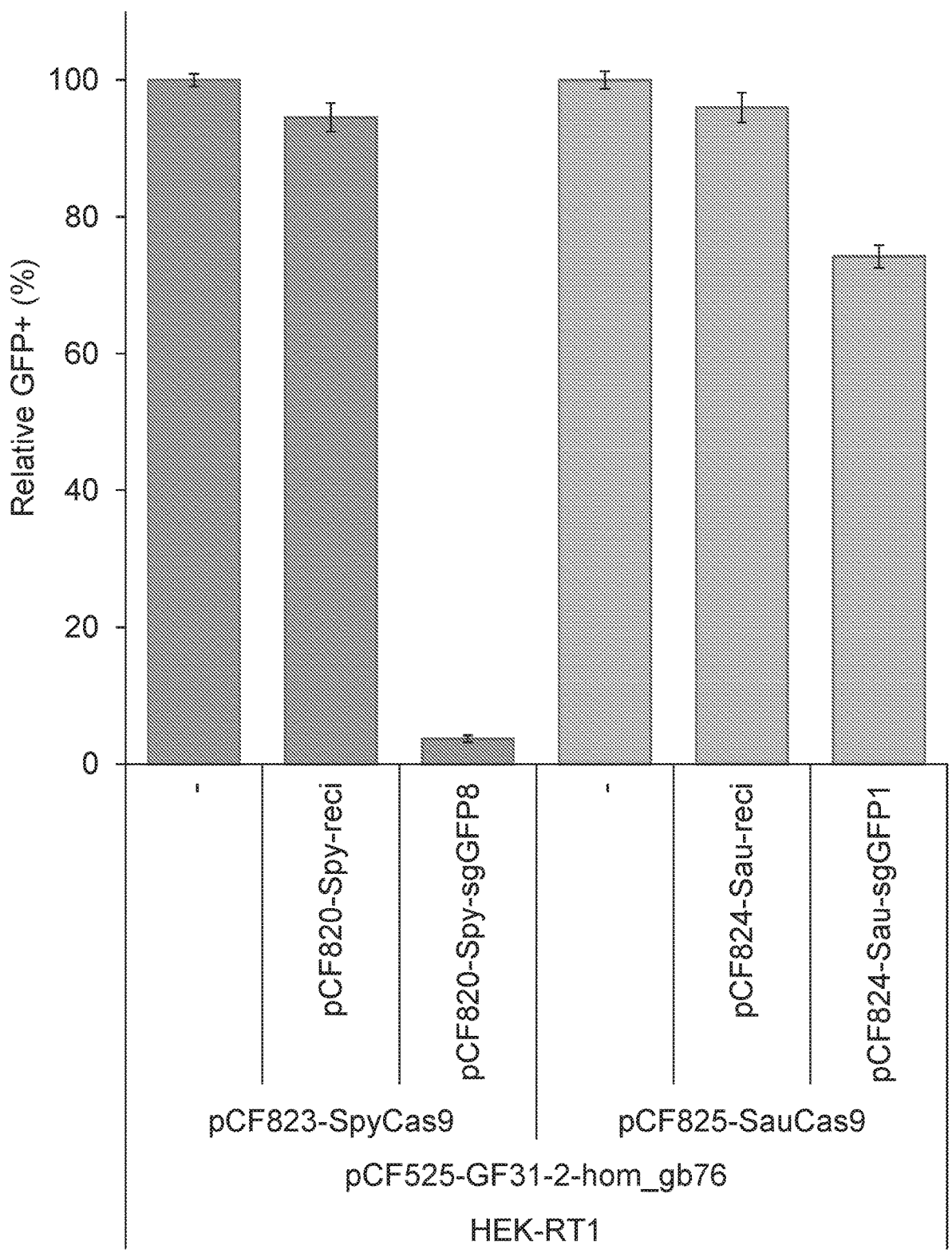
FIG. 16 depicts the effect of anti-CRISPR protein GF31-2-hom (gb76; homolog of GF31-cand2) on *S. pyogenes* (SpyCas9)/guide RNA-mediated and *S. aureus* (SauCas9)/guide RNA-mediated cleavage of a genomic target nucleic acid in a mammalian cell.

FIG. 16 depicts the effect of anti-CRISPR protein GF31-2-hom (gb76; homologue of GF31-cand2) on *S. pyogenes* (SpyCas9)/guide RNA-mediated and *S. aureus* (SauCas9)/guide RNA-mediated cleavage of a genomic target nucleic acid in a mammalian cell. The data show the efficiency of Acr-mediated inhibition of genomic GFP disruption by SpyCas9 or SauCas9 with a respective guide RNA targeting GFP, in a human cell line. The various Cas9 and guide RNAs were expressed from separate, stably integrated lentiviral vectors. The anti-CRISPR protein was expressed from a stably integrated lentiviral vector. The reporter GFP was expressed from a stably integrated lentiviral vector under control of a doxycycline-inducible promoter. GF31-2-hom inhibited SauCas9 but not SpyCas9 in mammalian cells; GF31-2-hom inhibited SauCas9 slightly less efficiently than GF31-cand2 and GF31-2-trunc in mammalian cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A fusion polypeptide comprising:

a) anti-CRISPR (Acr) polypeptide that is an inhibitor of an enzymatic activity of a Cas9 polypeptide, wherein the Acr polypeptide comprises an amino acid sequence having at least 90% amino acid sequence identity to the amino acid sequence set forth in SEQ ID NO: 12; and b) a heterologous fusion partner.

2. The fusion polypeptide of claim 1, wherein the heterologous fusion partner is a nuclear localization sequence.

3. The fusion polypeptide of claim 1, wherein the heterologous fusion partner is an epitope tag.

4. The fusion polypeptide of claim 1, wherein the Acr polypeptide has a length of from 125 amino acids to 134 amino acids.

5. A nucleic acid comprising a nucleotide sequence encoding the fusion polypeptide of claim 1.

6. A recombinant expression vector comprising the nucleic acid of claim 5.

7. A cell comprising the nucleic acid of claim 5.

8. A modified AcrIIA7 polypeptide comprising:

a) an AcrIIA7 polypeptide that is an inhibitor of an enzymatic activity of a Cas9 polypeptide, wherein the AcrIIA7 polypeptide comprises an amino acid sequence having at least 90% amino acid sequence identity to the amino acid sequence set forth in SEQ ID NO: 12; and b) a heterologous non-peptidic moiety covalently linked to the AcrIIA7 polypeptide.

9. The modified AcrIIA7 polypeptide of claim 8, wherein the non-peptidic moiety provides for one or more of an increase in in vivo half-life, in vivo stability, and bioavailability of the AcrIIA7 polypeptide, compared to the unmodified AcrIIA7 polypeptide.

10. A recombinant expression vector comprising a nucleotide sequence encoding an AcrIIA7 polypeptide that is an inhibitor of an enzymatic activity of a Cas9 polypeptide, wherein the AcrIIA7 polypeptide comprises an amino acid sequence having at least 90% amino acid sequence identity to the amino acid sequence set forth in SEQ ID NO: 12.

11. A cell comprising the recombinant expression vector of claim 10.

12. A recombinant expression vector comprising:
   a) a first nucleotide sequence encoding the constant region of a guide RNA;
   b) a second nucleotide sequence encoding a Cas9 polypeptide; and
   c) a third nucleotide sequence encoding an AcrIIA7 polypeptide that is an inhibitor of the Cas9 polypeptide, wherein the AcrIIA7 polypeptide comprises an amino acid sequence having at least 90% amino acid sequence identity to the amino acid sequence set forth in SEQ ID NO: 12.

13. The recombinant expression vector of claim 12, comprising an insertion site for inserting a nucleotide sequence encoding a guide sequence of the guide RNA, wherein the insertion site is 5' of and immediately adjacent to the first nucleotide sequence.

14. The recombinant expression vector of claim 12, comprising a nucleotide sequence encoding a guide sequence of the guide RNA, wherein the guide sequence-encoding nucleotide sequence is 5' of and immediately adjacent to the first nucleotide sequence.

15. The recombinant expression vector of claim 12, wherein the Cas9 polypeptide comprises an amino acid sequence having at least 70% amino acid sequence identity to the amino acid sequence depicted in SEQ ID NO: 3.

16. The recombinant expression vector of claim 12, wherein the third nucleotide sequence is operably linked to a promoter.

17. The recombinant expression vector of claim 16, wherein the promoter is functional in a eukaryotic cell.

18. The recombinant expression vector of claim 16, wherein the promoter is an inducible promoter.

19. The recombinant expression vector of claim 18, wherein the inducible promoter is a heat-inducible promoter, a drug-inducible promoter, an alcohol-inducible promoter, a hormone-inducible promoter, a steroid-inducible promoter, or a metal-inducible promoter.

20. The recombinant expression vector of claim 16, wherein the promoter is a tissue-specific promoter or a cell type-specific promoter.

21. A cell comprising the nucleic acid of claim 12.

22. A recombinant expression vector comprising a nucleotide sequence encoding an AcrIIA7 polypeptide that is an inhibitor of an enzymatic activity of a Cas9 polypeptide, wherein the AcrIIA7 polypeptide comprises an amino acid sequence having at least 90% amino acid sequence identity to the amino acid sequence set forth in SEQ ID NO: 12, and wherein the nucleotide sequence is optimized for expression in a mammalian cell.

* * * * *